US008796339B2

(12) United States Patent  
Schmaus et al.

(10) Patent No.: US 8,796,339 B2  
(45) Date of Patent: Aug. 5, 2014

(54) COMPOSITIONS COMPRISING BENZYL ALCOHOL DERIVATIVES AND FURTHER ANTIMICROBIAL ACTIVE COMPOUNDS

(75) Inventors: Gerhard Schmaus, Höxter (DE); Antje Pfeiffer, Holzminden (DE)

(73) Assignee: Symrise AG, Holzminden (DE)

( * ) Notice: Subject to any disclaimer, the term of this patent is extended or adjusted under 35 U.S.C. 154(b) by 309 days.

(21) Appl. No.: 13/003,404

(22) PCT Filed: Jul. 10, 2008

(86) PCT No.: PCT/EP2008/059037  
§ 371 (c)(1),  
(2), (4) Date: Feb. 28, 2011

(87) PCT Pub. No.: WO2008/119841  
PCT Pub. Date: Oct. 9, 2008

(65) Prior Publication Data  
US 2011/0152383 A1 Jun. 23, 2011

(51) Int. Cl.  
A61K 31/045 (2006.01)  
A01N 25/00 (2006.01)

(52) U.S. Cl.  
USPC .................... 514/730; 514/738; 424/405

(58) Field of Classification Search  
USPC .................. 514/730, 738; 424/405  
See application file for complete search history.

(56) References Cited

U.S. PATENT DOCUMENTS

| | | | |
|---|---|---|---|
| 5,539,001 A | 7/1996 | Waldmann-Laue et al. | |
| 7,582,681 B2 * | 9/2009 | Schmaus et al. ............ | 514/738 |
| 2003/0234382 A1 | 12/2003 | Sato et al. | |
| 2006/0106024 A1 | 5/2006 | Levy et al. | |

FOREIGN PATENT DOCUMENTS

| | | |
|---|---|---|
| CN | 1620248 A | 5/2005 |
| EP | 0524548 A1 | 1/1993 |
| EP | 1157687 A2 | 11/2001 |
| EP | 1369037 A1 | 12/2003 |
| JP | H06-509564 A | 10/1994 |
| JP | 2003-081711 A | 3/2003 |
| JP | 2006-143719 A | 6/2006 |
| JP | 2006188614 A | 7/2006 |
| WO | WO-93/01714 A1 | 2/1993 |
| WO | WO-03069994 A1 | 8/2003 |

OTHER PUBLICATIONS

Translation of EP 0524548.*  
Siegert, W., "The benefit of using synergistic mixtures of preservatives," Database Caplus [Online] Chemical Abstracts Service, Columbus, Ohio, US, retrieved from STN Database accession No. 2007: 246066 CAS-RN 672298-04-3, abstract & SOFW Journal, 132(12), 48, 50-52 Coden, XP002529501.

(Continued)

Primary Examiner — Renee Claytor  
(74) Attorney, Agent, or Firm — Novak Druce Connolly Bove + Quigg LLP

(57) ABSTRACT

The present invention relates to a composition comprising or consisting of:
(a) one, two or more compounds selected from the group consisting of benzyl alcohol derivatives of the formula (I)

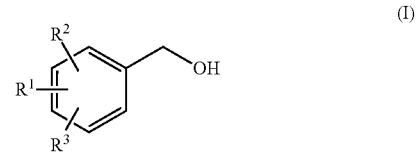

wherein each of the substituents $R^1$, $R^2$, and $R^3$ has a position at the aromatic ring, and wherein the substituents $R^1$, $R^2$, and $R^3$ independently of one another are selected from the group consisting of:
H; OH; $OCH_3$; COON;
linear or branched, saturated aliphatic hydrocarbon radical having 1 to 8 carbon atoms;
linear or branched, unsaturated aliphatic hydrocarbon radical having 2 to 8 carbon atoms;
$COOR^4$, wherein $R^4$ is a linear or branched alkyl radical having 1 to 8 carbon atoms;
wherein the total number of carbon atoms in substituents $R^1$, $R^2$ and $R^3$ is 1 to 12,
and
(b) one, two or more compounds selected from the group consisting of:
(i) branched or unbranched 1,2-alkanediols having 3 to 14 carbon atoms,
(ii) benzoic acid (INCI: Benzoic Acid) and its esters and salts,
(iii) 4-hydroxybenzoic acid and its esters (INCI: Parabens) and salts,
(iv) 2,4-hexadienoic acid (INCI: Sorbic Acid) and its salts,
(v) 2-phenoxyethanol (INCI: Phenoxyethanol)
(vi) 3-iodo-2-propinyl-butylcarbamate (INCI: Iodopropynyl Butylcarbamate),
(vii) 3-(4-chlorphenoxy)-1,2-propane-1,2-diol (INCI: Chlorphenesin),
(viii) urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxy-methylurea (INCI: Diazolidinyl Urea) and N-(4-chlorophenyl)-N'-(3,4-dichlorophenyl)-urea (INCI: Triclocarban),
(ix) 1,3-bis-(hydroxymethyl)-5,5-dimethyl-2,4-imidazolidindione (INCI: DMDM hydantoin),
(x) 1,2-propanediol, 3-(2-ethylhexyloxy) (INCI: Octoxyglycerin),
(xi) isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone).

16 Claims, No Drawings

(56) References Cited

OTHER PUBLICATIONS

Weber, K. et al., "Organic acids—a fashionable alternative for cosmetics preservation," Database Caplus [Online] Chemical Abstracts Services, Columbus, Ohio, US, retrieved from STN Database accession No. 2003: 744006 CAS-RN 672298-04-03, abstract & SOFW Journal, 129(6), 48, 50-52, 54-55, Coden, XP002529502.

International Search Report and Written Opinion from International Searching Authority, International Application No. PCT/EP2008/059037, filed Oct. 7, 2008.

Summary of Office Action, issued in parallel Japanese Application No. 2011-516970 on Jun. 28, 2013, together with the reporting letter from the Japanese patent associates.

Official Communication, Chinese Patent Application No. 2012111600788430, dated Nov. 21, 2012.

Office Action issued in parallel Chinese Application No. 200880130767.9 on Mar. 3, 2014.

Office Action issued in parallel Japanese Application No. 2011-516970 on Mar. 3, 2014 (together with the summary of the Office Action).

\* cited by examiner

COMPOSITIONS COMPRISING BENZYL ALCOHOL DERIVATIVES AND FURTHER ANTIMICROBIAL ACTIVE COMPOUNDS

CROSS-REFERENCE TO RELATED APPLICATIONS

This application is a National Phase filing under 35 U.S.C. §371 of PCT/EP2008/059037, filed Jul. 10, 2008, the entire contents of which is incorporated herein by reference.

The present invention relates to the field of antimicrobial actives, and in particular relates to certain (synergistic) antimicrobial compositions (mixtures) comprising or consisting of (a) at least one benzyl alcohol derivative as specified in more detail below and (b) at least one antimicrobial active compound selected from subgroups (i) to (xi) as specified in more detail below. The most preferred benzyl alcohol derivative is 4-methylbenzyl alcohol. As constituent of group (b) most preferred are 1,2-alkanediols having 3 to 14 carbon atoms. Other preferred compositions are described in more detail below and/or are defined in the attached set of claims.

The present invention further relates to the use of a composition according to the present invention for use in the treatment of germs, in particular for use in the treatment of *Aspergillus niger*.

Related aspects of the present invention concern the use of a composition according to the present invention for the preparation of a medicament for use in the treatment of germs, in particular for use in the treatment of *Aspergillus niger*.

A further aspect of the present invention relates to the use of (a) at least one benzyl alcohol derivative (as specified in more detail below) for synergistically intensifying the antimicrobial activity of certain antimicrobial actives (as specified in more detail below).

A corresponding method according to the present invention is a method for synergistically intensifying the antimicrobial activity of (b) one or more antimicrobial actives (as specified in more detail below), wherein said antimicrobial actives are mixed with an effective amount of (a) at least one benzyl alcohol derivative as specified in more detail below.

Even further, the present invention relates to a method for the preservation or antimicrobial treatment of a perishable product, wherein the perishable product is brought into contact with a composition according to the present invention.

All aspects of the present invention are based on the finding that it is possible to synergistically intensify the antimicrobial activity by combining at least one benzyl alcohol derivative of formula (I) (i.e. a compound of group (a)) (as specified below) with at least one compound of group (b), i.e. of sub-groups (i) to (xi) (as specified below).

All details and advantages of the present invention which are hereinafter explained with reference to the composition of the present invention apply mutatis mutandis to the other aspects of the present invention.

In the cosmetics, pharmaceutical, oral care and in the foodstuffs and beverages industry there is a constant need for agents having antimicrobial properties, in particular for the preservation of products which are otherwise perishable (such as e.g. cosmetics, pharmaceutical products, oral care products, foodstuffs and beverages), but also for direct cosmetic or therapeutic treatment of microorganisms which can have an adverse influence on the human or animal body. Reference may be made by way of example to microorganisms which can cause body odor, acne, dandruff, mycoses or the like.

In the technical fields referred to a large number of antimicrobial active compounds are indeed already employed, but alternatives nevertheless continue to be sought, in order to be able to perform targeted specific treatments and/or reduce side effects. In this context, however, in the search for alternative agents having an antimicrobial and in particular preserving action it is to be noted that the substances used in the cosmetics, pharmaceutical, foodstuffs and/or and beverages field must be
- toxicologically acceptable,
- readily tolerated by the skin,
- stable (in particular in the conventional cosmetic and/or pharmaceutical formulations),
- largely and preferably completely odorless and
- inexpensive to prepare (i.e. employing standard processes and/or starting from standard precursors).

The search for suitable (active) substances which have one or more of the properties mentioned to an adequate extent is made difficult for the person skilled in the art in that there is no clear dependency between the chemical structure of a substance on the one hand and its biological activity against certain microorganisms (germs) and its stability on the other hand. Furthermore, there is no predictable connection between the antimicrobial action, the toxicological acceptability, the skin tolerability and the stability of a substance.

*Aspergillus niger* is a mould which can be combated only with great difficulty. Although substances like 1,2-alkanediols having 3 to 14 carbon atoms are known to have a considerable activity against certain germs and microorganisms, in a number of cases the effect against *Aspergillus niger* is considered to be not sufficient.

It was therefore a general problem to be solved by the present invention to either provide for an alternative antimicrobial active having one or more of the above properties and being as effective against germs as a given known antimicrobial active, or to provide for an antimicrobial additive one or more of the above properties and capable of supplementing the antimicrobial properties of a given antimicrobial active so that the total antimicrobial activity of the combination of actives is (synergistically) increased, and so that in particular *Aspergillus niger* can be combated with good or improved reliability.

Favourably, the alternative antimicrobial active or the antimicrobial additive should be essentially or completely odorless in typical concentrations of use.

Even further, the antimicrobial effect of the alternative antimicrobial active or the effect of the combination of the antimicrobial additive with the known antimicrobial active against *Aspergillus niger* should preferably be so strong that a product comprising 1 wt.-% of the antimicrobial active or the combination should allow for a 3 log or at least 2 log reduction of germs within one week (see the examples section below for further details of test design etc.).

This problem is solved by a composition comprising or consisting of
(a) one, two or more compounds selected from the group consisting of benzyl alcohol derivatives of the formula (I)

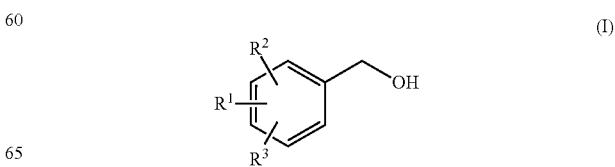

wherein each of the substituents $R^1$, $R^2$, and $R^3$ has a position at the aromatic ring, and wherein the substituents $R^1$, $R^2$, and $R^3$ independently of one another are selected from the group consisting of:
H; OH; OCH$_3$; COON;
linear or branched, saturated aliphatic hydrocarbon radical having 1 to 8 carbon atoms;
linear or branched, unsaturated aliphatic hydrocarbon radical having 2 to 8 carbon atoms;
COOR$^4$, wherein R$^4$ is a linear or branched alkyl radical having 1 to 8 carbon atoms;
wherein the total number of carbon atoms in substituents $R^1$, $R^2$ and $R^3$ is 1 to 12,
and
(b) one, two or more compounds selected from the group consisting of:
  (i) branched or unbranched 1,2-alkanediols having 3 to 14 carbon atoms,
  (ii) benzoic acid (INCI: Benzoic Acid) and its esters and salts,
  (iii) 4-hydroxybenzoic acid and its esters (INCI: Parabens) and salts,
  (iv) 2,4-hexadienoic acid (INCI: Sorbic Acid) and its salts,
  (v) 2-phenoxyethanol (INCI: Phenoxyethanol)
  (vi) 3-iodo-2-propinyl-butylcarbamate (INCI: Iodopropynyl Butylcarbamate),
  (vii) 3-(4-chlorphenoxy)-1,2-propane-1,2-diol (INCI: Chlorphenesin),
  (vii) urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxymethylurea (INCI: Diazolidinyl Urea) and N-(4-chlorophenyl)-N'-(3,4-dichlorophenyl)-urea (INCI: Triclocarban),
  (ix) 1,3-bis-(hydroxymethyl)-5,5-dimethyl-2,4-imidazolidindione (INCI: DMDM hydantoin),
  (x) 1,2-propanediol, 3-(2-ethylhexyloxy) (INCI: Octoxyglycerin),
  (xi) isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone).

The invention is based on the surprising finding that (a) benzyl alcohol derivatives of the formula (I) as stated above (as antimicrobial additive) synergistically increase the antimicrobial activity of (b) compounds selected from subgroups (i) to (xi) as stated above.

The antimicrobial mixtures according to the invention are suitable for preservation and antimicrobial treatment of perishable products, such as e.g. cosmetic products, pharmaceutical products, oral care products, foodstuffs and beverages.

The amounts and ratios of (a) the one or more benzyl alcohol derivatives of formula (I) and the one or more compounds of group (b) in the mixture according to the present invention are preferably adjusted such that their antimicrobial action is intensified synergistically according to Kull et al.; Applied Microbiology 9; p. 538-541 (1961), see also Steinberg; Cosmetics & Toiletries 115 (11); p. 59-62 (2000).später zu verschieben Preferably, in a composition according to the present invention, the only, one, two or more compounds of component (a) are selected from the group consisting of benzyl alcohol derivatives of said formula (I) wherein the substituents $R^1$, $R^2$, and $R^3$ independently of one another are selected from the group consisting of:
H; OH; OCH$_3$,
linear or branched, saturated aliphatic hydrocarbon radical having 1 to 6 carbon atoms.

Even more preferred are compositions according to the present invention, wherein the only, one, two or more compounds of component (a) are selected from the group consisting of benzyl alcohol derivatives of said formula (I) wherein the substituents $R^1$, $R^2$, and $R^3$ independently of one another are selected from the group consisting of:
H or linear or branched, saturated aliphatic hydrocarbon radical having 1 to 4 carbon atoms, and
wherein the total number of carbon atoms in substituents $R^1$, $R^2$, and $R^3$ is 1 to 8, preferably 1 to 4.

Even further, very preferred are compositions according to the present invention, wherein the only, one, two or more compounds of component (a) are selected from the group consisting of:
4-methylbenzyl alcohol,
3-methylbenzyl alcohol,
2-methylbenzyl alcohol,
2,4-dimethylbenzyl alcohol,
2,4,6-trimethylbenzyl alcohol,
4-ethylbenzyl alcohol,
3-ethylbenzyl alcohol,
2-ethylbenzyl alcohol.

In most preferred compositions according to the present invention, one or the only compound of component (a) is 4-methylbenzyl alcohol.

The structural formula of the most preferred compound 4-methylbenzyl alcohol (CAS-number 589-18-4; p-methylbenzyl alcohol, p-tolyl alcohol, p-tolyl carbinol), for use in a composition according to the invention, is:

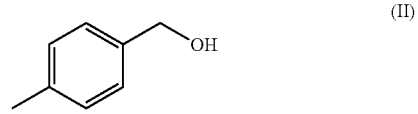

(II)

The concentration of component (a), i.e. the total concentration of compounds selected from the above defined group consisting of benzyl alcohol derivatives of the formula (I) (according to any of the above embodiments, in particular according to any of the embodiments characterized as being preferred) can vary and will largely depend on both the concentration of component (b) (total concentration of compounds selected from subgroups (i) to (xi)) and the concentration of further components. The skilled person will understand that in a composition consisting of or essentially consisting of components (a) and (b) the concentration of component (a) will be higher than in compositions comprising a large amount of further components besides components (a) and (b).

It is preferred that in compositions according to the present invention which comprise at least 50 wt.-% of further components besides (a) and (b), component (a) is present in an amount of from 0.05 to 0.50 wt.-%, preferably 0.10 to 0.30 wt.-%, based on the total weight of the composition.

In compositions according to the present invention which comprise no or at most 20 wt.-% of further components besides (a) and (b), component (a) is present in an amount of from 2 to 80 wt.-%, preferably 5 to 50 wt.-%, based on the total weight of component (b).

A very preferred composition according to the present invention (in particular a composition characterized hereinbefore as being preferred) is a composition, wherein the total amount of compounds of component (b) or the total amount of one or more or all compounds selected from one of sub-groups (i) to (xi) of component (b) is selected so as to synergistically intensify the antimicrobial activity of the total amount of compounds of component (a).

Within the present text an effect is considered as being synergistic if the requirements are met which are stated by Kull et al.; Applied Microbiology 9; p. 538-541 (1961), see also Steinberg; Cosmetics & Toiletries 115 (11); p. 59-62 (2000). As to the determination of synergy indices, see the examples section below.

Compositions according to the present invention comprise as component (b) one, two or more compounds selected from the group consisting of sub-groups (i) to (xi). The skilled person will understand that the amount of component (b) will depend on the compounds selected from sub-groups (i) to (xi), and their amounts.

In particular, compositions according to the present invention are preferred which comprise at least 50 wt.-% of further components besides (a) and (b), wherein component (a) is present in an amount of from 0.05 to 0.5 wt.-%, based on the total weight of the composition (see above). In particular with respect to such compositions according to the present invention it is preferred to use certain amounts of compounds of sub-groups (i) to (xi) so that the compounds of component (a) synergistically increase the effect of the selected compounds of component (b), i.e. sub-groups (i) to (xi).

Particularly preferred are compositions according to the present invention (in particular compositions comprising at least 50 wt.-% of further components besides (a) and (b)) comprising one, two or more compounds and total amounts as selected from the group consisting of
  (i) 0.1-5.0 wt.-% branched or unbranched 1,2-alkanediols having 3 to 14 carbon atoms,
  (ii) 0.1-1.0 wt.-% benzoic acid (INCI: Benzoic Acid) and its esters and salts,
  (iii) 0.1-0.8 wt.-% 4-hydroxybenzoic acid and its esters (INCI: Parabens) and salts,
  (iv) 0.1-0.6 wt.-% 2,4-hexadienoic acid (INCI: Sorbic Acid) and its salts,
  (v) 0.1-1.0 wt.-% 2-phenoxyethanol (INCI: Phenoxyethanol)
  (vi) 0.01-0.1 wt.-% 3-iodo-2-propinyl-butylcarbamate (INCI: Iodopropynyl Butylcarbamate),
  (vii) 0.02-0.2 wt.-% 3-(4-chlorphenoxy)-1,2-propane-1,2-diol (INCI: Chlorphenesin),
  (viii) 0.1-0.5 wt.-% urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxy-methylurea (INCI: Diazolidinyl Urea) and N-(4-chlorophenyl)-N'-(3,4-dichlorophenyl)-urea (INCI: Triclocarban),
  (ix) 0.1-0.6 wt.-% 1,3-bis-(hydroxymethyl)-5,5-dimethyl-2,4-imidazolidindione (INCI: DMDM hydantoin),
  (x) 0.1-1.0 wt.-% 1,2-propanediol, 3-(2-ethylhexyloxy) (INCI: Octoxyglycerin),
  (xi) 0.00015-0.0015 wt.-% isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone),
based on the total weight of the composition.

In particular, compositions according to the present invention (in particular compositions as described above as being preferred) are preferred, wherein for one or more sub-groups (i) to (xi) of component (b) the ratio $r_{a/b}$ of the total weight of component (a) to the total weight of compounds of said sub-groups of component (b) is in the range of from
  (i) 1:100 to 5:1, preferably 1:20 to 1:1, for the total weight of branched or unbranched 1,2-alkanediols having 3 to 14 carbon atoms,
  (ii) 1:20 to 5:1, preferably 1:5 to 2:1, for the total weight of benzoic acid (INCI: Benzoic Acid) and its esters and salts,
  (iii) 1:16 to 5:1, preferably 1:4 to 2:1, for the total weight of 4-hydroxybenzoic acid and its esters (INCI: Parabens) and salts,
  (iv) 1:12 to 5:1, preferably 1:3 to 2:1, for the total weight of 2,4-hexadienoic acid (INCI: Sorbic Acid) and its salts,
  (v) 1:20 to 5:1, preferably 1:2 to 5:1, for the total weight of 2-phenoxyethanol (INCI: Phenoxyethanol)
  (vi) 1:2 to 50:1, preferably 1:1 to 20:1, for the total weight of 3-iodo-2-propinylbutylcarbamate (INCI: Iodopropynyl Butylcarbamate),
  (vii) 1:4 to 25:1, preferably 1:2 to 10:1, for the total weight of 3-(4-chlorphenoxy)-1,2-propane-1,2-diol (INCI: Chlorphenesin),
  (viii) 1:12 to 5:1, preferably 1:3 to 2:1, for the total weight of urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxy-methylurea (INCI: Diazolidinyl Urea) and N-(4-chlorophenyl)-N'-(3,4-dichlorophenyl)-urea (INCI: Triclocarban),
  (ix) 1:12 to 5:1, preferably 1:3 to 2:1, for the total weight of 1,3-bis-(hydroxymethyl)-5,5-dimethyl-2,4-imidazolidindione (INCI: DMDM hydantoin),
  (x) 1:20 to 5:1, preferably 1:5 to 2:1, for the total weight of 1,2-propanediol, 3-(2-ethylhexyloxy) (INCI: Octoxyglycerin),
  (xi) 33:1 to 3333:1, preferably 100:1 to 1000:1, for the total weight of isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone).

For the preparation of an effective composition according to the invention which in particular causes a significant reduction in the *Aspergillus niger* germ count, it is generally sufficient to mix an amount of one or more compounds of component (a) with an amount of one or more compounds of component (b). The ratios of components (a) and (b) depend on the maximum use levels of compounds of component (b), as indicated above. Preferred embodiments are summarized in the following table.

| Antimicrobial Agents | Use level range [weight-%] | Use level ratio: group (a): group (b) | Prefered use level range: group (a): group (b) |
| --- | --- | --- | --- |
| 1,2-Alkanediols | 0.1-5.0 | 1:100 to 5:1 | 1:20 to 1:1 |
| Benzoic Acid | 0.1-1.0 | 1:20 to 5:1 | 1:5 to 2:1 |
| Parabens | 0.1-0.8 | 1:16 to 5:1 | 1:4 to 2:1 |
| Sorbic Acid | 0.1-0.6 | 1:12 to 5:1 | 1:3 to 2:1 |
| Phenoxyethanol | 0.1-1.0 | 1:20 to 5:1 | 1:2 to 5:1 |
| Chlorphenesin | 0.02-0.2 | 1:4 to 25:1 | 1:2 to 10:1 |
| Imidazolidinyl urea | 0.1-0.6 | 1:12 to 5:1 | 1:3 to 2:1 |
| Diazolidinyl Urea | 0.1-0.5 | 1:10 to 5:1 | 1:3 to 2:1 |
| DMDM hydantoin | 0.1-0.6 | 1:12 to 5:1 | 1:3 to 2:1 |
| Octoxyglycerin | 0.1-1.0 | 1:20 to 5:1 | 1:5 to 2:1 |

-continued

| Antimicrobial Agents | Use level range [weight-%] | Use level ratio: group (a): group (b) | Prefered use level range: group (a): group (b) |
|---|---|---|---|
| Iodopropynyl Butylcarbamate | 0.01-0.1 | 1:2 to 50:1 | 1:1 to 20:1 |
| Methylchloro-isothiazolinone and Methyliso-thiazolinone | 0.00015-0.0015 | 33:1 to 3333:1 | 100:1 to 1000:1 |

The present invention is in particular (but not exclusively) based on the surprising finding that compositions according to the present invention show a synergistically intensified antimicrobial effect at least against selected germs, and in particular at least against *Aspergillus niger*, a mould which can be combated only with great difficulty.

In particular, it has been now been found that the compositions according to the present invention can be used outstandingly as an antimicrobial active compound mixture (composition), in particular for preserving otherwise perishable articles (see the initial remarks above and the more detailed description below).

The use of 4-methylbenzyl alcohol in cosmetic products, especially in hair conditioning and hair dying products as solvent is described in WO 2004/014327, U.S. Pat. No. 6,248, 314, DE 43 42 075, WO 94/02111, EP 0 547 790 and GB 2259717.

Although antimicrobial properties of 4-methylbenzyl alcohol and other substituted benzyl alcohol derivatives, of alkanediols, and of other substances now used in the compositions of the present invention have been addressed and described in the literature, there has hitherto been no indication that compositions according to the present invention could have a significantly improved antimicrobial action (at least against selected germs).

Structure activity correlations and studies on the antimicrobial action of certain benzyl alcohol derivatives of formula (I) are reported in the literature.

J. Chem. Inf. Comput. Sci. 1997 (37), 320-328 and J. Pharmaceutical Sciences Vol. 1980, 69, 1034-1039 report calculated activities of some benzyl alcohol derivatives of formula (I), including 4-methylbenzyl alcohol, against *Aspergillus niger* and compare these to those known from J. Pharm. Pharmacol., Suppl. 1958, 10, 149T.

The use of benzyl alcohol derivatives of formula (I) in combination with compounds of group (b) as antimicrobial active composition is not disclosed in the prior art, in particular not for use in cosmetic products.

As to the compounds of sub-groups (i) to (xi) of component (b) of compositions according to the present invention, various documents describe antimicrobial activity of the compounds per se. Regarding combinations of 1,2-alkanediols with further antimicrobially active substances, EP 1 206 933, WO 03/069994 and WO 2006/082151 may be mentioned by way of example. However, compositions according to the present invention and their antimicrobial activity, in particular against *Aspergillus niger*, are not disclosed in the prior art.

1,2-alkanediols generally have only a deficient action against moulds such as *Aspergillus niger*. With respect to individual 1,2-alkanediols and their mixtures, a gap in the activity is recorded with respect to moulds, in particular with respect to the "problem germ" *Aspergillus niger*. For complete inhibition of moulds like *Aspergillus niger* high use concentrations of individual 1,2-alkanediols and their mixtures are necessary.

In particular, a synergistic intensification in antimicrobial activity by combination of (a) one, two or more benzyl alcohol derivatives of formula (I), in particular 4-methylbenzyl alcohol, with (b) (i) branched or unbranched 1,2-alkane diols having 3 to 14 carbon atoms is not disclosed in the prior art.

It was particularly surprising that compositions according to the present invention show a highly synergistic activity, and in the treatment of *Aspergillus niger* are significantly superior to individually dosed benzyl alcohol derivatives of formula (I) and mixtures of benzyl alcohols of the formula (I), in particular of 4-methylbenzyl alcohol of formula (II), individually dosed branched or unbranched 1,2-alkanediols having 3 to 14 carbon atoms, in particular branched or unbranched 1,2-alkanediols having 3 to 10 carbon atoms, and chosen from this group in particular 1,2-pentanediol, 1,2-hexanediol, 1,2-octanediol, 1,2-decanediol and mixtures thereof, at the same concentration, in particular with respect to the reduction in germ count and the speed of the reduction in germ count.

In view of the significant intensification in the antimicrobial action of their respective components, compositions according to the present invention are particularly suitable for combating *Aspergillus niger* even at low concentration.

With respect to the compounds of sub-groups (ii) to (xi) the situation is similar as with respect to the branched or unbranched 1,2-alkanediols having 3 to 14 carbon atoms of sub-group (ii) of component (b) of a composition according to the present invention.

In a preferred embodiment, component (b) of the composition according to the present invention comprises or consists of one, two or more compounds selected from the group consisting of (i) branched or unbranched 1,2-alkanediols having 3 to 10 carbon atoms.

In particular, it is preferred to select the branched or unbranched 1,2-alkanediols having 3 to 10 carbon atoms from the group consisting of 1,2-propanediol, 1,2-butanediol, 1,2-pentanediol, 1,2-hexanediol, 1,2-octanediol, 1,2-decanediol, and mixtures thereof.

The use of mixtures of said 1,2-alkanediols is in particular preferred.

Particularly preferred compositions of the present invention component (b) comprise or consist of
(i) mixtures of branched or unbranched 1,2-alkanediols having 3 to 10 carbon atoms, the mixtures being selected from the group consisting of:
a mixture of 1,2-propanediol and 1,2-butanediol,
a mixture of 1,2-propanediol and 1,2-pentanediol,
a mixture of 1,2-propanediol and 1,2-hexanediol,
a mixture of 1,2-propanediol and 1,2-octanediol,
a mixture of 1,2-propanediol and 1,2-decanediol,
a mixture of 1,2-butanediol and 1,2-pentanediol,
a mixture of 1,2-butanediol and 1,2-hexanediol,
a mixture of 1,2-butanediol and 1,2-octanediol,
a mixture of 1,2-butanediol and 1,2-decanediol,
a mixture of 1,2-pentanediol and 1,2-hexanediol,
a mixture of 1,2-pentanediol and 1,2-octanediol,
a mixture of 1,2-pentanediol and 1,2-decanediol,
a mixture of 1,2-hexanediol and 1,2-octanediol,
a mixture of 1,2-hexanediol and 1,2-decanediol,
a mixture of 1,2-octanediol and 1,2-decanediol,
a mixture of 1,2-propanediol, 1,2-pentanediol and 1,2-hexanediol,
a mixture of 1,2-propanediol, 1,2-pentanediol and 1,2-octanediol, a mixture of 1,2-propanediol, 1,2-hexanediol and 1,2-octanediol, a mixture of 1,2-pentanediol, 1,2-hexanediol and 1,2-octanediol, a mixture of 1,2-pentanediol, 1,2-octanediol and 1,2-decanediol, a mixture of 1,2-hexanediol, 1,2-octanediol and 1,2-decanediol, a mixture of 1,2-propanediol, 1,2-pentanediol, 1,2-hexanediol and 1,2-octanediol, and a mixture of 1,2-pentanediol, 1,2-hexanediol, 1,2-octanediol and 1,2-decanediol.

It is preferred that in such a composition component (a) comprises or consists of 4-methylbenzyl alcohol.

In a preferred composition according to the present invention component (a) comprises or consists of 4-methylbenzyl alcohol, and component (b) comprises or consists of a mixture of two different 1,2-alkanediols, preferably of a mixture of 1,2-hexanediol and 1,2-octanediol.

Preferred compositions of the present invention comprise two different 1,2-alkanediols, preferably two different 1,2-alkanediols, preferably a mixture of 1,2-hexanediol and 1,2-octanediol, in a weight ratio of from 10:1 to 1:10, preferably of from 5:1 to 1:5.

Preferred are also compositions of the present invention comprising three different 1,2-alkanediols in a weight ratio of from (10 to 60):(10 to 60):(10 to 60), preferably in the range of from (15 to 50):(15 to 50):(15 to 50).

Preferred compositions can of course be a cosmetic, pharmaceutical, or care product, a foodstuff or a beverage.

A particularly preferred composition according to the present invention comprises 4-methylbenzyl alcohol in a mixture with 1,2-hexanediol and 1,2-octanediol, in a weight ratio of from (1 to 2):(1 to 2):(2 to 4), preferably (1 to 1.2):(1 to 1.2):(2.9 to 3.1).

In a composition comprising both 1,2-hexanediol and 1,2-octanediol as well as 4-methylbenzyl alcohol the weight ratio of 4-methylbenzyl alcohol to the total amount of 1,2-hexandediol and 1,2-octanediol is preferably in the range of from 1:1 to 1:10, more preferably in the range of from 1:2 to 1:6.

As an example, if a composition according to the present invention comprises a total amount of 8 parts by weight of one or more 1,2-alkanediols (in particular 1,2-hexanediol and/or 1,2-octanediol), the total amount of benzyl alcohol derivatives of formula (I), in particular the total amount of 4-methylbenzyl alcohol, would preferably be in the range of 0.5 to 5 parts by weight, preferably 1 to 3 parts by weight. The concentration of components (a) and (b) in the composition of the present invention depends on the further components that are present in the composition.

Compositions according to the present invention can be products of various fields. If e.g. a composition of the present invention essentially consists of components (a) and (b), so that the total amount of further components is at most 20 wt.-%, based on the total weight of the composition, such compositions can be used for preservation and antimicrobial treatment of perishable products, such as e.g. cosmetic products, pharmaceutical products, oral care products, foodstuffs, and beverages.

On the other hand, compositions according to the present invention can be selected from the group consisting of cosmetic, pharmaceutical and oral care products, foodstuffs and beverages. In this case, the composition preferably comprises at least 50 percent by weight, typically at least 94 percent by weight, of further components besides (a) and (b), based on the total weight of the composition. If a perishable product is to be preserved, it is brought into contact with an antimicrobially active amount of a composition according to the present invention, preferably with an amount which is active against *Aspergillus niger*.

Compositions according to the present invention can advantageously be combined, in particular in cosmetic formulations (compositions), with further conventional components, such as, for example:

further preservatives, in particular those described in US 2006/0089413, antimicrobial agents, such as e.g. antibacterial agents or agents to treat yeast and mold, in particular those described in WO 2005/123101, antiacne and sebum reducing agents, in particular those described in WO 2008/046791, compounds against ageing of the skin, in particular those described in WO 2005/123101, antidandruff agents, in particular those described in WO 2008/046795, antiirritants (antiinflammatory agents, irritation-preventing agents, irritation-inhibiting agents), in particular those described in WO 2007/042472 and US 2006/0089413, antioxidants, in particular those described in WO 2005/123101, carrier materials, in particular those described in WO 2005/123101, chelating agents, in particular those described in WO 2005/123101, deodorizing agents and antiperspirants, in particular those described in WO 2005/123101, moisture regulators (moisture-donating agents, moisturizing substance, moisture-retaining substances), in particular those described in WO 2005/123101, osmolytes, in particular those described in WO 2005/123101, compatible solutes, in particular those described in WO 01/76572 and WO 02/15868, proteins and protein hydrolysates, in particular those described in WO 2005/123101, skin-lightening agents, in particular those described in WO 2007/110415, skin-tanning agents, in particular those described in WO 2006/045760, cooling agents, in particular those described in WO 2005/123101, skin-cooling agents, in particular those described in WO 2005/123101, warming agents, in particular those described in WO 2005/123101, UV-absorbing agents, in particular those described in WO 2005/123101, UV filters, in particular those described in WO 2005/123101, benzylidene-beta-dicarbonyl compounds in accordance with WO 2005/107692 and alpha-benzoyl-cinnamic acid nitriles in accordance with WO 2006/015954, insect repellents, in particular those described in WO 2005/123101, plant parts, plant extracts, in particular those described in WO 2005/123101, vitamins, in particular those described in WO 2005/123101, emulsifiers, in particular those described in WO 2005/123101, gelling agents, in particular those described in WO 2005/123101, oils in particular those described in WO 2005/123101, waxes in particular those described in WO 2005/123101, fats in particular those described in WO 2005/123101, phospholipids, in particular those described in WO 2005/123101, saturated fatty acids and mono- or polyunsaturated fatty acids and α-hydroxy acids and polyhydroxy-fatty acids and esters of saturated and/or unsaturated branched and/or unbranched alkane carboxylic acids, in particular those described in WO 2005/123101, surface-active substances (surfactants) in particular those described in WO 2005/123101, skin repair agents comprising cholesterol and/or fatty acids and/or ceramides and/or pseudoceramides, in particular those described in WO 2006/053912, dyestuffs and colorants and pigments, in particular those described in WO 2005/123101, aroma chemicals and flavors and fragrances, in particular those described in S. Arctender, Perfume and Flavor Chemicals, private publishing house, Montclair, N.J., 1969 and Surburg, Panten, Common Fragrance and Flavor Materials, 5th Edition, Wiley-VCH, Weinheim 2006, preferably those explicitly mentioned in US 2008/0070825, alcohols and polyols, in particular those described in WO 2005/123101, organic solvents, in particular those described in WO 2005/123101, silicones and silicone oils and silicone derivatives, virucides, abrasives, anti-cellulite agents, astringents, antiseptic agents, antistatics, binders, buffers, cell stimulants, cleansing agents, care agents, depilatory agents, softeners, enzymes, essential oils, in particular those described in US 2008/0070825, fibres, film-forming agents, fixatives, foam-forming agents, foam stabilizers, substances for preventing foaming, foam boosters, gel-forming agents, hair growth activators, hair growth inhibitors, hair care agents, hair-setting agents, hair-straightening agents, hair-smoothening, bleaching agents, strengthening agents, stain-removing agents, optically brightening agents, impregnating agents, dirt-repellent agents, friction-reducing agents, lubricants, opacifying agents, plasticizing agents, covering agents, polish, gloss agents, polymers, powders, peptides, mono-, di- and oligosaccharides, re-oiling agents, abrading agents, skin-soothing agents, skin-cleansing agents, skin care agents, skin-healing agents, skin-protecting agents, skin-softening agents, skin-smoothing agents, nourishing agents, skin-warming agents, stabilizers, detergents, fabric conditioning agents, suspending agents, thickeners, yeast extracts, algae or microalgae extracts, animal extracts, liquefiers, color-protecting agents, anticorrosives and electrolytes.

It was already mentioned above that agents having an antimicrobial and in particular preserving action should preferably be odorless. However, benzyl alcohol derivatives of formula (I) sometimes show an odor (although when compared to most fragrance compounds a rather weak odor) when used at concentration levels of e.g. 1.5 or 2 wt. %, e.g. in a cosmetic or pharmaceutical formulation. Such concentrations are necessary if a given benzyl alcohol derivative of formula (I) is used for combating *Aspergillus niger* on its own, i.e. not in combination with other antimicrobial actives. The odor from benzyl alcohol derivatives of formula (I) is clearly perceivable at such concentration levels with bitter almond and benzaldehyd-like odor facettes which are not desired in most cases (vide supra: odorless actives are preferred).

In particular, from S. Arctander, Perfume and Flavor Chemicals, Montclair, N.J., 1969 it is known that:
2-methylbenzyl alcohol (o-tolyl alcohol) has a mild, floral, overall rosy, but also musty and sweet odor (n° 2957),
4-methylbenzyl alcohol (p-tolyl alcohol) has a faint, green-rosy, leafy and sweet-balsamic odor (n° 2958).

Thus, it was surprising that according to the present invention, benzyl alcohol derivatives of formula (I) can still play an important role in combating *Aspergillus niger* (as well as other germs). The surprising finding is based on the fact that said benzyl alcohol derivatives of formula (I) do not have to be used in the high amounts needed when germs like *Aspergillus niger* are to be combated by the alcohol derivatives of formula (I) on their own, if said alcohol derivatives of formula (I) are combined with the compounds of component (b) of the present invention. In the compositions of the present invention, the benzyl alcohol derivatives of formula (I) are not used primarily as an antimicrobial agent being effective on its own, but rather they are used as an antimicrobial additive synergistically intensifying and enhancing the antimicrobial activity of the compounds of component (b). Correspondingly, in the compositions of the present invention, the odor of the benzyl alcohol derivatives of formula (I) (e.g. the odor of 4-methylbenzyl alcohol) is not considered as being negative.

It is a considerably surprising result of the present invention that it is possible to achieve a modification of the odor imparted by benzyl alcohol derivatives of formula (I) used as anti microbial agent by incorporation of the benzyl alcohol derivatives into products of the present invention, i.e. by mixing said benzyl alcohol derivatives with other antimicrobial actives selected from sub-groups (i) to (xi) so that the amount of benzyl alcohol derivatives can be reduced and the overall product has an improved, less typical tolyl alcohol, bitter almond and benzaldehyde like odor.

Preferably, a composition of the present invention in addition to components (a) and (b) comprises a sensorially active amount of one or more fragrances of group (F) as stated below. The presence of such fragrances leads to compositions (e.g. mixtures or other products) having improved odor properties. In particular relevant is the presence of one or more fragrances of group (F) in cosmetic compositions according to the present invention. In such cases, further components are generally present in the composition.

Group (F) of fragrances, from which one or more fragrances can be selected for combination with components (a) and (b) consists of (in the following list in some cases the normal industrial product names and registered trademarks of various firms are stated):
alpha-hexylcinnamaldehyde,
p-tert-butyl cyclohexyl acetate,
cis-3-hexenyl acetate,
allyl amyl glycolate,
coumarin,
dihydromyrcenol(2,6-dimethyl-7-octen-2-ol),
methyl dihydrojasmonate (preferably with a content of cis-isomers of >60 by weight, available unter the names Hedione or Hedione HC),
4,6,6,7,8,8-hexamethyl-1,3,4,6,7,8-hexahydrocyclopenta[g] benzopyran (Galaxolide),
tetrahydrolinalool(3,7-dimethyloctan-3-ol),
benzyl salicylate,
2-methyl-3-(4-tert-butyl-phenyl)propanal (Lilial),
cinnamic alcohol,
4,7-methano-3a,4,5,6,7,7a-hexahydro-5-indenyl acetate and/or 4,7-methano-3a,4,5,6,7,7a-hexahydro-6-indenyl acetate (Herbaflorat),
styrolyl acetate (1-phenylethyl acetate),
octahydro-2,3,8,8-tetramethyl-2-acetonaphthone and/or 2-acetyl-1,2,3,4,6,7,8-octahydro-2,3,8,8-tetramethylnaphthalene (Iso E Super),
hexyl salicylate,
4-tert.-butylcyclohexyl acetate (Oryclon),
2-tert.-butylcyclohexyl acetate (Agrumex HC),
alpha-ionone(4-(2,2,6-trimethyl-2-cyclohexen-1-yl)-3-buten-2-one),
terpinyl acetate,
4-(4-hydroxy-4-methylpentyl)-3-cyclohexene carboxaldehyde (Lyral),
alpha-amylcinnamaldehyde,
(E)- and/or (Z)-3-methylcyclopentadec-5-enone (Muscenon),
15-pentadec-11-enolide and/or 15-pentadec-12-enolide (Globalide),
15-cyclopentadecanolide (Macrolide),
1-(5,6,7,8-tetrahydro-3,5,5,6,8,8-hexamethyl-2-naphthalenyl)ethanone (Tonalide),
2-ethyl-4-(2,2,3-trimethyl-3-cyclopenten-1-yl)-2-buten-1-ol (Sandranol),
menthol (preferably l-menthol or racemic menthol, with particular preference for l-menthol),
anethole,
geraniol,
linalool,
citronellol,
linalyl acetate,
2-phenylethyl alcohol, rose oxide (4-methyl-2-(2-methyl-1-propenyl)tetrahydropyran),
allyl heptanoate,
4-methylacetophenone,
1-(2,2,6-trimethylcyclohexyl)hexan-3-ol (Timberol),
2,4,6-trimethyl-4-phenyl-1,3-dioxane (Floropal),
benzylacetone,
methyl cinnamate,
ethylene brassylate,
3a,6,6,9a-tetramethyldodecahydronaphtho[2,1-b]furan (Ambroxid).

Correspondingly, compositions are preferred comprising components (a) and (b) as defined above (preferably components (a) and (b) characterized above as being preferred), and in addition one, two or more fragrance compounds selected from group (F).

Such a preferred composition according to the present invention is preferably a cosmetic, pharmaceutical or oral care product, a foodstuff or a beverage, cosmetic products being particularly preferred.

It has also been found that compositions according to the invention in particular cosmetic products, comprising a sensorially active amount of one or more of the fragrances of group (F) lead to mixtures and products having improved odor properties.

Further preferred are compositions of the present invention comprising three, four, five or more of the fragrances selected from group (F) as stated above. Such combinations can demonstrate an improved odor effect, see the examples section below.

Preferably the fragrances of group (F) are selected from the group consisting of:
alpha-hexylcinnamaldehyde,
cis-3-hexenyl acetate,
allyl amyl glycolate,
dihydromyrcenol,
methyl dihydrojasmonate,
4,6,6,7,8,8-hexamethyl-1,3,4,6,7,8-hexahydrocyclopenta[g]benzopyran,
tetrahydrolinalool,
2-methyl-3-(4-tert-butyl-phenyl)propanal,
octahydro-2,3,8,8-tetramethyl-2-acetonaphthone,
2-acetyl-1,2,3,4,6,7,8-octahydro-2,3,8,8-tetramethylnaphthalene,
hexyl salicylate,
4-(4-hydroxy-4-methylpentyl)-3-cyclohexene carboxaldehyde,
alpha-amylcinnamaldehyde,
(E)- and/or (Z)-3-methylcyclopentadec-5-enone,
15-cyclopentadecanolide,
1-(5,6,7,8-tetrahydro-3,5,5,6,8,8-hexamethyl-2-naphthalenyl)ethanone,
2-ethyl-4-(2,2,3-trimethyl-3-cyclopenten-1-yl)-2-buten-1-ol,
l-menthol,
geraniol,
linalool,
citronellol,
linalyl acetate,
2-phenylethyl alcohol,
4-methylacetophenone,
benzylacetone,
methyl cinnamate, and
ethylene brassylate.

In preferred compositions according to the present invention, in particular in cosmetic compositions, the total amount of the (preferred) fragrances from group (F) is in the range of from 0.01 to 1.5 wt.-%, more preferably in the range of from 0.05 to 1.0 wt.-%, most preferably in the range of from 0.1 to 0.75 wt.-%, based on the total weight of the composition.

Preferred compositions of the present invention (in particular cosmetic compositions) include, in particular for a further improved effectiveness, one or more adjuvants selected from group (H) consisting of:
dipropylene glycol (DPG), diethyl phthalate (DEP), triethyl citrate (TEC), isopropyl myristate (IPM), and benzyl benzoate (BB).

Also preferred are compositions according to the present invention comprising one or more cooling agents selected from the group consisting of: menthol, preferably l-menthol, menthone glycerin acetal (trade name: Frescolat®MGA), menthyl lactate (preferably l-menthyl lactate, in particular l-menthyl-l-lactate, trade name: Frescolat®ML), substituted menthyl-3-carboxylic acid amide (e.g. menthyl-3-carboxylic acid-N-ethylamide), 2-isopropyl-N-2,3-trimethylbutanamide, substituted cyclohexane carboxylic acid amide, 3-menthoxypropane-1,2-diol, 2-hydroxyethylmenthylcarbonate, 2-hydroxypropylmenthylcarbonate, N-acetyl glycine menthyl ester, Isopulegol, menthyl hydroxycarboxylic acid ester (e.g. menthyl-3-hydroxybutyrate), monomenthylsuccinate, 2-mercaptocyclodecanone, menthyl-2-pyrrolidin-5-one carboxylate, 2,3-dihydroxy-p-menthane, 3,3,5-trimethyl cyclohexanone glycerine ketal, 3-menthyl-3,6-di- and -trioxalkanoate, 3-menthylmethoxy acetate, N-(4-cyanomethylphenyl)-p-menthanecarboxamide, N-(4-cyanophenyl)-p-menthanecarboxamide and Icilin.

Preferred cooling agents are: l-menthol, menthone glycerine acetal (trade name: Frescolat®MGA), menthyl lactate (preferably l-menthyl lactate, in particular l-menthyl-l-lactate, trade name: Frescolat®ML), 3-menthoxy propane-1,2-diol, 2-hydroxyethyl menthyl carbonate, 2-hydroxypropyl menthyl carbonate, particular preference being for l-menthyl-l-lactate.

Compositions according to the present invention may comprise one or more compatible solutes. Preferred compatible solutes are described in WO 01/76572, namely dimyoinositol phosphate (DIP), diglycerin phospate (DGP), di-myo-inositol phosphate (DIP), cyclic 2,3 diphosphoglycerate (cDPG), 1,1-di-glycerol phosphate (DGP), beta-mannosyl glycerate (firoin), beta-mannosyl glyceramide (firoin-A) and di-mannosyl-di-inositol phosphate (DMIP) and ectoine and ectoine-derivatives, as described in EP 0 553 884, EP 0 671 161 and WO 94/15923, in particular ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid).

Preferably, the total amount of compatible solutes is in the range of from 0.05 to 10 wt.-%, preferably 0.1 to 5 wt.-%, based on the total weight of the formulation according to the present invention.

Compositions according to the present invention may comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis*, licorice, grape, apple, barley or hops or/nd hydrolysates from rice or wheat.

Compositions according to the present invention may comprise one or more hair growth inhibitors, i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre*.

Compositions according to the present invention may comprise one or more anti-cellulite agents as well as agents enhancing or boosting the activity of anti-cellulite agents.

Anti-cellulite agents and lipolytic agents are preferably selected from the group consisting of those described in WO 2007/077541, and beta-adrenergic receptor agonists such as synephrine and its derivatives.

Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

For certain applications compositions according to the present invention are preferred which in addition to components (a) and (b), in particular in addition to 1,2-alkanediols of component (b) (i), comprise one, two or more compounds of the group consisting of:
glycerol, 1,3-propanediol, 1,3-butanediol, 1,4-butanediol, 2,3-butanediol, 1,5-pentanediol, 1,6-hexanediol, 1,8-octanediol, 2-methylpentane-2,4-diol, 2,5-hexanediol, 3,6-octanediol, 2-ethyl-1,3-hexanediol, 1,3-octanediol, and 1,3-decanediol.

In particular, such compositions can be cosmetic, pharmaceutical or oral compositions, food stuffs or beverages.

If a composition according the present invention is to be used for preserving organic material, or if a composition according to the present invention in addition to components (a) and (b) comprises an organic material which is to be preserved, the composition preferably comprises one or more preservatives which do not belong to components (a) and (b). Such additional preservatives are preferably selected from the group consisting of:
propionic acid and its esters and salts, salicylic acid and its esters and salts, formaldehyde and paraformaldehyde, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, 4-chloro-m-cresol, 2,4,4'-trichloro-2'-hydroxy-diphenyl ether (triclosan), 1-(4-chlorophenoxy)-3,3-dimethyl-1-(imidazole-1-yl)-2-butanone (climbazole), 1-hydroxy-4-methyl-6-(2,4,4-trimethylpentyl)-2(1H)-pyridone, 2-aminoethanol (Octopirox®), 4-chloro-3,5-dimethylphenol, poly-(hexamethylenediguanide) hydrochloride, hexamethylenetetramine, 1-(3-chloroallyl)-3,5,7-triaza-1-azonia-adamantane chloride, 1,2-dibromo-2,4-dicyanobutane, 2,2'-methylene-bis(6-bromo-4-chlorophenol), bromochlorophene, 2-benzyl-4-chlorophenol, 2-chloroacetamide, chlorhexidine, chlorhexidine acetate, chlorhexidine gluconate, chlorhexidine hydrochloride, tropolone, N-alkyl($C_{12}$-$C_{22}$)trimethylammonium bromide and chloride, 4,4-dimethyl-1,3-oxazolidine, 1,6-bis(4-amidinophenoxy)-n-hexane and its salts, glutaraldehyde, 5-ethyl-1-aza-3,7-dioxabicyclo(3.3.0)octane, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzylammonium saccharinate, benzyl alcohol, benzyl hemiformal, sodium hydroxymethyl-aminoacetate or sodium hydroxymethyl-aminoacetate, sodium hydroxymethylglycinate and polyaminopropyl biguanide, benzethonium chloride, 2-bromo-2-nitropropane-1,3-diol, and (different) salts or solvates thereof.

Compositions of the present invention in addition to components (a) and (b) may additionally comprise further known antimicrobials like chitosan, totarol, farnesol, glycerol monolaurate, arylalkyl alcohols, such as e.g. 4-methyl-4-phenyl-2-pentanol and its derivatives (DE 101 43 434, in particular 4-methyl-4-phenyl-2-pentanol), muguet alcohol (2,2-dimethyl-3-phenylpropanol), other arylalkyl alcohols (e.g. as disclosed in DE 44 47 361, DE 103 30 697, U.S. Pat. No. 4,110,430 or EP 1 157 687), 2-butyloctanoic acid, 2-hexyldecanoic acid, p-anisic acid, essential oils with antimicrobial properties and isolates from essential oils with antimicrobial properties like e.g. thymol or eugenol, perfume oils or single aroma chemicals with antimicrobial activity, polyglycerol esters, such as e.g. polyglyceryl 3-caprylates, or combinations of the substances mentioned, which are generally employed, inter alia, against underarm odor, foot odor, acne or dandruff formation.

Compositions according to the present invention because of their synergistically intensified antimicrobial activity can in particular be employed
(a) for the cosmetic treatment of microorganisms which cause body odor (including underarm odor, foot odor),
(b) for the cosmetic treatment of microorganisms which cause acne,
(c) for the cosmetic treatment of microorganisms which cause mycoses (d) for the cosmetic treatment of microorganisms which cause dandruff
(e) for the treatment of microorganisms on or in inanimate matter.

The compositions according to the invention display their synergistically intensified antimicrobial action against a large number of Gram-positive bacteria, Gram-negative bacteria, moulds and yeasts. A particularly good action exists against *Propionibacterium acnes*, Gram-positive bacteria such as *Staphylococcus aureus, Staphylococcus epidermidis, Corynebacterium xerosis*, Gram-negative bacteria, such as *Escherichia coli* and *Pseudomonas aeruginosa*, against yeasts, such as *Candida albicans, Malassezia* species (e.g. *Malassezia furfur*), *Epidermophyton* species (e.g. *Epidermophyton floccosum*), *Trichophyton* species (e.g. *Trichophyton rubrum*) and precisely—as already mentioned—against fungi, such as *Aspergillus niger*. The very good activity of the compositions according to the invention against *Aspergillus niger*, a mould which can be combated only with great difficulty, is to be regarded as particularly advantageous here.

The present invention also relates to compositions of the present invention as a medicament, i.e. relates to the finding that compositions according to the present invention can be used for the therapeutic treatment of germs (as listed above).

Additionally, the invention also relates to compositions of the present invention for use in the treatment of germs, in particular for use in the treatment of *Aspergillus niger*.

Even further, the present invention relates to the use of compositions according to the present invention for the preparation of a medicament for use in the treatment of germs, in particular for use in the treatment of *Aspergillus niger*.

The invention also relates to the use of compositions according to the present invention as antimicrobial active compositions.

As explained above, teachings regarding preferred embodiments of compositions according to the present invention apply mutatis mutandis to uses of compositions according to the present invention, and corresponding methods.

The present invention also relates to the use of (a) one, two or more compounds selected from the group consisting of benzyl alcohol derivatives of the formula (I)

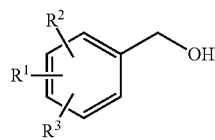

(I)

wherein each of the substituents $R^1$, $R^2$, and $R^3$ has a position at the aromatic ring, and wherein the substituents $R^1$, $R^2$, and $R^3$ independently of one another are selected from the group consisting of:
H; OH; OCH$_3$; COON;
linear or branched, saturated aliphatic hydrocarbon radical having 1 to 8 carbon atoms;
linear or branched, unsaturated aliphatic hydrocarbon radical having 2 to 8 carbon atoms;
COOR$^4$, wherein $R^4$ is a linear or branched alkyl radical having 1 to 8 carbon atoms;
wherein the total number of carbon atoms in substituents $R^1$, $R^2$ and $R^3$ is 1 to 12,
for synergistically intensifying the antimicrobial activity of (b) one, two or more compounds selected from the group consisting of:
(i) branched or unbranched 1,2-alkanediols having 3 to 14 carbon atoms,
(ii) benzoic acid (INCI: Benzoic Acid) and its esters and salts,
(iii) 4-hydroxybenzoic acid and its esters (INCI: Parabens) and salts,
(iv) 2,4-hexadienoic acid (INCI: Sorbic Acid) and its salts,
(v) 2-phenoxyethanol (INCI: Phenoxyethanol)
(vi) 3-iodo-2-propinyl-butylcarbamate (INCI: Iodopropynyl Butylcarbamate),
(vii) 3-(4-chlorphenoxy)-1,2-propane-1,2-diol (INCI: Chlorphenesin),
(viii) urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxymethylurea (INCI: Diazolidinyl Urea) and N-(4-chlorophenyl)-N'-(3,4-dichlorophenyl)-urea (INCI: Triclocarban),
(ix) 1,3-bis-(hydroxymethyl)-5,5-dimethyl-2,4-imidazolidindione (INCI: DMDM hydantoin),
(x) 1,2-propanediol, 3-(2-ethylhexyloxy) (INCI: Octoxyglycerin),
(xi) isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone).

Correspondingly, the invention also relates to a method for synergistically intensifying the antimicrobial activity of
(b) one, two or more antimicrobially active compounds selected from the group consisting of:
(i) branched or unbranched 1,2-alkanediols having 3 to 14 carbon atoms,
(ii) benzoic acid (INCI: Benzoic Acid) and its esters and salts,
(iii) 4-hydroxybenzoic acid and its esters (INCI: Parabens) and salts,
(iv) 2,4-hexadienoic acid (INCI: Sorbic Acid) and its salts,
(v) 2-phenoxyethanol (INCI: Phenoxyethanol)
(vi) 3-iodo-2-propinyl-butylcarbamate (INCI: Iodopropynyl Butylcarbamate),
(vii) 3-(4-chlorphenoxy)-1,2-propane-1,2-diol (INCI: Chlorphenesin),
(viii) urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxymethylurea (INCI: Diazolidinyl Urea) and N-(4-chlorophenyl)-N'-(3,4-dichlorophenyl)-urea (INCI: Triclocarban),
(ix) 1,3-bis-(hydroxymethyl)-5,5-dimethyl-2,4-imidazolidindione (INCI: DMDM hydantoin),
(x) 1,2-propanediol, 3-(2-ethylhexyloxy) (INCI: Octoxyglycerin),
(xi) isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone)
comprising the following step:
mixing an amount of one, two or more compounds of said antimicrobially active compounds with an effective amount of (a) one, two or more compounds selected from the group consisting of benzyl alcohol derivatives of the formula (I)

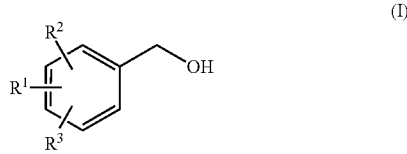

wherein each of the substituents $R^1$, $R^2$, and $R^3$ has a position at the aromatic ring, and wherein the substituents $R^1$, $R^2$, and $R^3$ independently of one another are selected from the group consisting of:
H; OH; $OCH_3$; COON;
linear or branched, saturated aliphatic hydrocarbon radical having 1 to 8 carbon atoms;
linear or branched, unsaturated aliphatic hydrocarbon radical having 2 to 8 carbon atoms;
$COOR^4$, wherein $R^4$ is a linear or branched alkyl radical having 1 to 8 carbon atoms;
wherein the total number of carbon atoms in substituents $R^1$, $R^2$ and $R^3$ is 1 to 12.

The invention also relates to a method for the preservation or antimicrobial treatment of a perishable product, with the following step:
bringing the perishable product into contact with an antimicrobially active amount, preferably an amount which is active against *Aspergillus niger*, of a composition according to the present invention.

The present invention furthermore relates to corresponding methods for the cosmetic and/or therapeutic treatment of germs, and in particular especially of (a) microorganisms which cause body odor, (b) microorganisms which cause acne (c) microorganisms which cause mycoses, (d) microorganisms which cause dandruff, comprising topical application of an antimicrobially active amount of a composition according to the invention, the amount of said diols and benzyl alcohol derivatives in the composition preferably being adjusted such that their antimicrobial action is synergistically intensified.

Preferred embodiments of the methods and uses according to the present invention correspond to the preferred embodiments of the compositions according to the present invention, which are explained above and below.

The human skin is populated by a large number of various microorganisms, which include the microorganisms already mentioned above, as well as others. Most of these microorganisms are not pathogenic and are irrelevant to the physiological state of the skin and to the odor thereof. On the other hand, others can influence the healthy state of the skin decisively.

As similarly explained above, the synergistically active compositions of the present invention have a good antimicrobial activity not only against *Aspergillus niger* but also against *Staphylococcus epidermidis, Corynebacterium xerosis, Brevibacterium epidermidis, Propionibacterium acnes* and against *Trichophyton* and *Epidermophyton* species, so that they can also be employed as agents for the treatment of (combating) underarm and foot odor or body odor generally, as agents for combating acne, as antidandruff agents and for the treatment of mycoses (in particular dermatomycoses).

In the context of the present text, "treatment" is understood as meaning any form of influencing of the microorganisms in question in which the multiplication of these microorganisms is inhibited and/or the microorganisms are killed.

The total amount of components (a) and (b) in compositions of the present invention, in particular in cosmetic, pharmaceutical or oral care products or in a foodstuff or beverage, is preferably in the range of from 0.01 to 10 wt.-%, but particularly preferably in the range of from 0.05 to 5 wt.-%, based on the total weight of the product, foodstuff or beverage.

As mentioned above, particularly preferred insofar are compositions wherein component (a) is present in an amount of from 0.05% to 0.5% by weight, preferably 0.1 to 0.3% by weight, based on the total weight of the composition.

It should again be noted that due to the synergistically enhanced antimicrobial activity of the compositions according to the present invention, the total amount of component (a) can be in the range of from 0.05 to 0.5 wt.-%, based on the total weight of the product, foodstuff or beverage. This is advantageous since such a reduced amount of compounds of group (a) results in a reduced odor impression stemming therefrom.

The product, foodstuff or beverage comprises conventional further constituents, in this context see below. The particular content of components (a) and/or (b) to be used according to the invention in compositions according to the invention can be below the amount regarded as antimicrobially active in itself if the total amount of these substances which is present is sufficiently high to achieve an antimicrobial action of the total mixture. This applies in particular to the action against *Aspergillus niger*.

The invention also relates to a method for the cosmetic and/or therapeutic treatment of (a) microorganisms which cause body odor, (b) microorganisms which cause acne and/or (c) microorganisms which cause mycoses (d) microorganisms which cause dandruff, wherein said microorganisms are brought into contact with an antimicrobially active amount of a composition according to the present invention. The total amount of components (a) and (b) of the composition used within the method of the present invention is preferably in the range of from 0.01 to 10 wt.-%, and particularly preferred in the range of from 0.05 to 5 wt.-%, based on the total weight of the (cosmetic or pharmaceutical) composition which comprises the mixture of components (a) and (b).

The compositions according to the present invention, comprising the synergistically active mixture of components (a) and (b), can be employed prophylactically or as required.

The total amount of components (a) and (b) to be applied, i.e. the total amount of the composition according to the present invention to be applied e.g. daily, varies and depends on the physiological state of the subject and individual-specific parameters, such as age or body weight. Within a composition according to the present invention, the mixture of components (a) and (b) can be employed either by themselves or in combination with further antimicrobially active substances.

It is to be pointed out that the 1,2-alkanediols of sub-group (b) (i) in compositions according to the present invention can be in the form of either the corresponding enantiomer of 2S configuration or the enantiomer of 2R configuration and in the form of any desired mixture of these enantiomers of 2S and 2R configuration. For commercial reasons, it is indeed particularly advantageous to employ, for combating microorganisms, racemates of the particular 1,2-alkanediols to be employed (or mixtures of two or more racemates), since the racemates are particularly readily accessible by synthesis, but the pure enantiomers or non-racemic mixtures of these enantiomers are likewise suitable for the purposes according to the invention.

Further uses/methods and mixtures/compositions according to the invention can be found in the following statements and the attached patent claims.

Compositions comprising components (a) and (b), especially if employed against germs which cause body odor, are as a rule applied topically in the form of solutions, creams, lotions, gels, sprays or the like. For other purposes, an oral (tablets, capsules, powders, drops), intravenous, intraocular, intraperitoneal or intramuscular administration or an administration in the form of an impregnated dressing is appropriate in some cases.

Mixtures of components (a) and (b) can be incorporated without difficulties into the usual cosmetic and/or dermatological formulations, such as, inter alia, pump sprays, aerosol sprays, creams, ointments, tinctures, lotions, nail care products (e.g. nail varnishes, nail varnish removers, nail balsams) and the like. It is also possible here, and in some cases advantageous, to combine the mixture of components (a) and (b) with further active compounds, for example with other antimicrobially, antimycotically or antivirally active substances. Cosmetic and/or dermatological/keratological compositions (formulations) comprising components (a) and (b) can otherwise have the conventional chemical composition, and might serve for the treatment of skin and/or hair in the sense of a dermatological treatment or a treatment in the sense of care cosmetics. However, compositions of the present invention can also be employed in make-up products in decorative cosmetics.

In compositions of the present invention, components (a) and (b) can moreover also particularly advantageously be employed in combination with perspiration-inhibiting active compounds (antiperspirants) for combating body odor. Perspiration-inhibiting active compounds which can be employed are, above all, aluminium salts, such as aluminium chloride, aluminium hydrochloride, nitrate, sulfate, acetate etc. In addition, however, the use of compounds of zinc, magnesium and zirconium may also be advantageous. For use in cosmetic and dermatological antiperspirants, the aluminium salts and—to a somewhat lesser extent—aluminium/zirconium salt combinations have essentially proved suitable. The aluminium hydroxychlorides which are partly neutralized and therefore tolerated better by the skin, but not quite so active, are additionally worth mentioning.

In compositions of the present invention, if components (a) and (b) are used for antimicrobial treatment of a surface (e.g. of a human or animal body), a combination with (metal) chelators is advantageous in some cases. (Metal) chelators which are preferably to be employed here are, inter alia, α-hydroxy fatty acids, phytic acid, lactoferrin, α-hydroxy acids, such as, inter alia, citric acid, lactic acid and malic acid, and humic acids, bile acids, bile extracts, bilirubin, biliverdin or EDTA, EGTA and derivatives thereof.

Compositions according to the present invention in the form of cosmetic and/or dermatologically active compositions are applied to the skin and/or hair in a sufficient amount in the conventional manner for cosmetics and dermatics. In this context, cosmetic and dermatological compositions which comprise components (a) and (b) and additionally act as sunscreen compositions offer particular advantages. These compositions (formulations) advantageously comprise at least one UVA filter and/or at least one UVB filter and/or at least one inorganic pigment. In this context, the compositions can be in various forms such as are conventionally employed e.g. for sunscreen formulations. They can be e.g. a solution, an emulsion of the water-in-oil (W/O) type or of the oil-in-water (O/W) type or a multiple emulsion, for example of the water-in-oil-in-water (W/O/W) type, a gel, a hydrodispersion, a solid stick or also an aerosol.

As mentioned, compositions which comprise components (a) and (b) can advantageously be combined with substances which absorb UV radiation, the total amount of the filter substances being e.g. 0.01 to 40 wt.-%, preferably 0.1 to 10 wt.-%, in particular 1.0 to 5.0 wt.-%, based on the total weight of the formulations, in order to provide cosmetic compositions which protect the hair or skin from ultraviolet radiation.

It is known in the art that preserving aqueous sunscreen formulations containing a relatively high amount of organic UV filters (and mostly a relatively high sun protection factor (SPF), typically a SPF of about 15 and higher) is very difficult, especially against yeasts, in particular *Candida* yeasts (cf. U.S. Pat. No. 5,292,529). Hitherto it is not quite understood why such sunscreen formulations have these preserving problems.

It has now been found that the compositions of the present invention, comprising components (a) and (b) in a mixture, in particular compositions comprising 4-methylbenzyl alcohol, preferably in combination with 1,2-pentanediol, 1,2-hexanediol, 1,2-octanediol and 1,2-decanediol or mixtures of said 1,2-alkanediols have also an excellent antimicrobial activity against yeasts, in particular against *Candida albicans* and moulds, in particular against *Aspergillus niger*.

Preferred compositions of the present invention are sunscreen formulations in the form of aqueous emulsions, preferably of the water-in-oil (W/O) or of the oil-in-water (O/W) type or a multiple emulsion, for example of the water-in-oil-in-water (W/O/W) type, more preferably of the oil-in-water (O/W) type.

Preferred sunscreen formulations (compositions) of the present invention comprise a total amount of organic UV filters of greater than 10 wt.-%, preferably in the range of from 12 to 40 wt.-%, more preferred in the range of from 15 to 35 wt.-%, based on the total weight of the sunscreen formulation.

In this context advantageous organic UV filters are:
p-aminobenzoic acid
p-aminobenzoic acid ethyl ester (25 mol) ethoxylated
p-dimethylaminobenzoic acid-2-ethylhexyl ester
p-aminobenzoic acid ethyl ester (2 mol) N-propoxylated
p-aminobenzoic acid glycerol ester
salicylic acid homomenthyl ester (homosalates) (Neo Heliopan®HMS)
salicylic acid-2-ethylhexyl ester (Neo Heliopan®OS)
triethanolamine salicylate
4-isopropyl benzyl salicylate
anthranilic acid menthyl ester (Neo Heliopan®MA)
diisopropyl cinnamic acid ethyl ester
p-methoxycinnamic acid-2-ethylhexyl ester (Neo Heliopan®AV)
diisopropyl cinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-ethylhexyl-2-cyano-3,3-diphenyl acrylate (Neo Heliopan®303)
ethyl-2-cyano-3,3'-diphenyl acrylate
2-phenylbenzimidazole sulfonic acid and salts (Neo Heliopan®Hydro)
3-(4'-trimethylammonium)benzylidene bornan-2-one methyl sulfate terephthalylidene dibornane sulfonic acid and salts (Mexoryl®SX)
4-t-butyl-4'-methoxydibenzoyl methane (avobenzone)/(Neo Heliopan®357)
β-imidazole-4(5)-acrylic acid (urocanic acid)
2-hydroxy-4-methoxybenzophenone (Neo Heliopan®BB)
2-hydroxy-4-methoxybenzophenone-5-sulfonic acid
dihydroxy-4-methoxybenzophenone
2,4-dihydroxybenzophenone
tetrahydroxybenzophenone
2,2'-dihydroxy-4,4'-dimethoxybenzophenone
2-hydroxy-4-n-octoxybenzophenone
2-hydroxy-4-methoxy-4'-methyl benzophenone
3-(4'-sulfo)benzylidene bornan-2-one and salts
3-(4'-methyl benzylidene)-d,l-camphor (Neo Heliopan®MBC)
3-benzylidene-d,l-camphor
4-isopropyl dibenzoyl methane
2,4,6-trianilino-(p-carbo-2'-ethylhexyl-1'-oxy)-1,3,5-triazine
phenylene bis-benzimidazyl tetrasulfonic acid disodium salt (Neo Heliopan®AP)
2,2'-(1,4-phenylene)-bis-(1H-benzimidazole-4,6-disulfonic acid), monosodium salt
N-[(2 and 4)-[2-(oxoborn-3-ylidene)methyl]benzyl]acrylamide polymer
phenol,-(2H-benzotriazol-2-yl)-4-methyl-6-(2-methyl-3 (1,3,3,3-tetramethyl-1-(trimethylsilyl)oxy)disiloxanyl)propyl), (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb®HEB)
2,2'-methylene bis-(6-(2H-benzotriazol-2-yl)-4-1,1,3,3-tetramethylbutyl)phenol), (Tinosorb®M)
2,4-bis-[4-(2-ethylhexyloxy)-2-hydroxyphenyl]-1,3,5-triazine
benzylidene malonate polysiloxane (Parsol®SLX)
glyceryl ethyl hexanoate dimethoxycinnamate
disodium-2,2'-dihydroxy-4,4'-dimethoxy-5,5'-disulfobenzophenone
dipropylene glycol salicylate
sodium hydroxymethoxybenzophenone sulfonate
4,4',4-(1,3,5-triazine-2,4,6-triyltriimino)-tris-benzoic acid tris(2-ethylhexyl ester) (Uvinul®T150)
2,4-bis-[{(4-(2-ethylhexyloxy)-2-hydroxy}phenyl]-6-(4-methoxyphenyl)-1,3,5-triazine (Tinosorb®S)
2,4-bis-[{(4-(3-sulfonato)-2-hydroxypropyloxy)-2-hydroxy}phenyl]-6-(4-methoxyphenyl)-1,3,5-triazine sodium salt
2,4-bis-[{(3-(2-propyloxy)-2-hydroxypropyloxy)-2-hydroxy}phenyl]-6-(4-methoxyphenyl)-1,3,5-triazine
2,4-bis-[{4-(2-ethyl hexyloxy)-2-hydroxy}phenyl]-6-[4-(2-methoxyethyl carbonyl)phenylamino]-1,3,5-triazine
2,4-bis-[{4-(3-(2-propyloxy)-2-hydroxypropyloxy)-2-hydroxy}phenyl]-6-[4-(2-ethylcarboxyl)phenylamino]-1,3,5-triazine
2,4-bis-[{4-(2-ethylhexyloxy)-2-hydroxy}phenyl]-6-(1-methylpyrrol-2-yl)-1,3,5-triazine
2,4-bis-[{4-tris-(trimethylsiloxysilylpropyloxy)-2-hydroxy}phenyl]-6-(4-methoxyphenyl)-1,3,5-triazine
2,4-bis-[{4-(2''-methylpropenyloxy)-2-hydroxy}phenyl]-6-(4-methoxyphenyl)-1,3,5-triazine
2,4-bis-[{4-(1',1',1',3'5',5',5'-heptamethylsiloxy-2''-methylpropyloxy)-2-hydroxy}phenyl]-6-(4-methoxyphenyl)-1,3,5-triazine
2-(4-diethylamino-2-hydroxybenzoyl)benzoic acid hexyl ester (Uvinul® A Plus)
indanylidene compounds in accordance with DE 100 55 940 (=WO 02/38537)

Organic UV filters which are particularly preferred in compositions of the present invention (in particular if they are in the form of a sunscreen formulation), preferably in an amount mentioned (above), are:
p-aminobenzoic acid
3-(4'-trimethylammonium)benzylidene bornan-2-one methyl sulfate
salicylic acid homomenthyl ester (Neo Heliopan®HMS)
2-hydroxy-4-methoxybenzophenone (Neo Heliopan®BB)
2-phenylbenzimidazole sulfonic acid (Neo Heliopan®Hydro)
terephthalylidene dibornane sulfonic acid and salts (Mexoryl®SX)
4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid-2-ethylhexyl ester (Neo Heliopan®AV)
p-aminobenzoic acid ethyl ester (25 mol) ethoxylated
p-methoxycinnamic acid isoamyl ester (Neo Heliopan E1000)
2,4,6-trianilino-(p-carbo-2'-ethylhexyl-1'-oxy)-1,3,5-triazine (Uvinul®T150)
phenol,2-(2H-benzotriazol-2-yl)-4-methyl-6-(2-methyl-3 (1,3,3,3-tetramethyl-1-(trimethylsilyl)oxy)disiloxanyl)propyl), (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-d,l-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine, (Tinosorb®S)
benzylidene malonate polysiloxane (Parsol®SLX)
menthyl anthranilate (Neo Heliopan®MA)
2-(4-diethylamino-2-hydroxybenzoyl) benzoic acid hexyl ester (Uvinul® A Plus)
indanylidene compounds in accordance with DE 100 55 940 (=WO 02/38537)

Compositions according to the present invention in the form of sunscreen formulations preferably have a SPF (sun protection factor) of equal or greater than 15, preferably of equal or greater than 20, more preferably of equal or greater than 30.

Preferred compositions of the present invention in the form of sunscreen formulations comprise 4-(1,1-dimethylethyl)-4'-methoxydibenzoylmethane(4-t-butyl-4'-methoxydibenzoyl methane; avobenzone), preferably in an amount in the range of from 0.2-10 wt.-%, more preferred in the range of from 0.5-5 wt.-%, based on the total weight of the sunscreen formulation.

In preferred sunscreen formulations comprising components (a) and (b) the pH-value is in the range of from pH 4 to pH 8, preferably from pH 4 to 6.5.

In compositions of the present invention in the form of formulations for topical prophylactic or cosmetic treatment of the skin a high content of care substances is generally advantageous. According to a preferred embodiment, the compositions comprise one or more animal and/or plant fats and oils having care properties, such as olive oil, sunflower oil, refined soya oil, palm oil, sesame oil, rapeseed oil, almond oil, borage oil, evening primrose oil, coconut oil, shea butter, jojoba oil, sperm oil, beef tallow, neat's foot oil and lard, and optionally further care constituents, such as, for example, fatty alcohols having 8 to 30 carbon atoms.

In compositions according to the present invention, care substances can be combined in an outstanding manner with the admixture of components (a) and (b). Such care substances include
- ceramides, where ceramides are understood as meaning N-acylsphingosins (fatty acid amides of sphingosin) or synthetic analogues of such lipids (so-called pseudoceramides), which significantly improve the water retention capacity of the stratum corneum.
- phospholipids, for example soya lecithin, egg lecithin and cephalins
- vaseline, paraffin oils and silicone oils; the latter include, inter alia, dialkyl- and alkylarylsiloxanes, such as dimethylpolysiloxane and methylphenylpolysiloxane, as well as alkoxylated and quaternized derivatives thereof.

Compositions of the present invention which are cosmetic compositions (formulations) in some cases preferably comprise antioxidants. All antioxidants can be used which are suitable or usual for cosmetic and/or dermatological uses.

Cosmetic compositions of the present invention which comprise an admixture of components (a) and (b) can additionally comprise vitamins and vitamin precursors. All vitams and vitamin precursors can be used which are suitable or usual for cosmetic and/or dermatological uses. In particular can be used vitamins and vitamin precursors such as tocopherols, vitamin A, niacic acid and niacinamide, further vitamins of the B complex, in particular biotin, and vitamin C and panthenol and derivatives thereof, in particular the esters and ethers of panthenol and cationically derivatized panthenols, such as e.g. panthenol triacetate, panthenol monoethyl ether and the monoacetate thereof and cationic panthenol derivatives.

Cosmetic compositions of the present invention can also comprise antiinflammatory or redness- or itching-alleviating active compounds. All antiinflammatory or redness- and itching-alleviating active compounds can be used which are suitable or usual for cosmetic and/or dermatological uses.

Cosmetic compositions of the present invention can also comprise active compounds having a skin-lightening or skin-tanning action. All skin-lightening or skin-tanning active compounds can be used which are suitable or usual for cosmetic and/or dermatological uses.

Cosmetic compositions according to the present invention can also comprise anionic, cationic, nonionic and/or amphoteric surfactants, especially if crystalline or microcrystalline solids, for example inorganic micropigments, are to be incorporated into the composition.

EXAMPLES

The present invention is explained further with the aid of the following non-limiting examples, illustrating the parameters of and compositions employed within the present invention. Unless stated otherwise, all data, in particular percentages, parts and ratios are by weight unless otherwise indicated.

Abbreviations used: DPG: dipropylene glycol, IPM: isopropyl myristate.

Example 1a

Comparison of adequate preservation of cosmetic formulations comprising a mixture of 1,2-hexanediol and 1,2-octanediol (product A, not according to the invention), 4-methylbenzyl alcohol (product B, not according to the invention) and a mixture of 1,2-hexanediol, 1,2-octanediol and 4-methylbenzyl alcohol (product C, according to the invention)

Testing for adequate preservation was carried out in accordance with the European Pharmacopoeia.

Testing thus comprises contamination of the formulation, if possible in its final condition, with a prescribed inoculum of suitable microorganisms, storage of the inoculated formulation at a certain temperature, removal of samples from the container at certain intervals of time and determination of the number of microorganisms in the samples removed in this way. The preserving properties are adequate if, under the conditions of the test, a clear reduction or, where appropriate, no increase in the germ count results in the inoculated formulations after the prescribed times at the prescribed temperatures. Experimental details of the test procedure are described in the European Pharmacopoeia (ISBN 3-7692-2768-9; Supplement 2001 to the 3rd Edition, page 421-422, chapter 5.1.3).

Test Germs:

The following microorganism strains were used for the tests for adequate preservation:
A: *Escherichia coli* ATCC 8739
B: *Pseudomonas aeruginosa* ATCC 9027
C: *Staphylococcus aureus* ATCC 6538
D: *Candida albicans* ATCC 10231
E: *Aspergillus niger* ATCC 16404

The initial germ count (cfu/ml; "0 value") was in the range of from 230000 to 400000 in the various test series.

Formulation:

For the tests for adequate preservation, a defined amount of the active compound combination according to the invention (product C) was incorporated into an O/W emulsion. For comparison purposes, the comparison products (product A and B) were incorporated into separate O/W emulsions.

Formulations with Products A, B and C:

TABLE 1a

| | INCI name | Manufacturer | A wt.-% | B wt.-% | C (inventive) wt.-% |
|---|---|---|---|---|---|
| Phase A | | | | | |
| Dracorin CE | Glyceryl Stearate Citrate | Symrise | 4.0 | 4.0 | 4.0 |
| PCL Solid | Stearyl Heptanoate, Stearyl Caprylate | Symrise | 3.0 | 3.0 | 3.0 |

TABLE 1a-continued

| | INCI name | Manufacturer | A wt.-% | B wt.-% | C (inventive) wt.-% |
|---|---|---|---|---|---|
| Paraffin oil °E | Paraffinum Liquidum | Parafluid | 7.0 | 7.0 | 7.0 |
| Lanette 18 | Stearyl Alcohol | Cognis | 1.5 | 1.5 | 1.5 |
| Dracorin GMS | Glyceryl Stearate | Symrise | 1.5 | 1.5 | 1.5 |
| Dow Corning 200 fluid | Dimethicone | Dow Corning | 2.0 | 2.0 | 2.0 |
| Phase B | | | | | |
| Water, demineralized | Water (Aqua) | | to 100 | to 100 | to 100 |
| Carbopol ETD 2050 Polymer | Carbomer | Noveon | 0.15 | 0.15 | 0.15 |
| 1,2-Hexanediol | 1,2-Hexanediol | Symrise | 0.5 | — | 0.4 |
| 1,2-Octanediol | Caprylyl Glycol | Symrise | 0.5 | — | 0.4 |
| 4-Methylbenzyl alcohol | not INCI listed | Symrise | — | 1.0 | 0.2 |
| Phase C | | | | | |
| Neutralizer AMP-95 | Amino Methylpropanol | Dow/Angus | 0.1 | 0.1 | 0.1 |
| Total: | | | 100.0 | 100.0 | 100.0 | pH 5.5

Result:

The results of the preservative stress tests for *Aspergillus niger* for the active compound combinations investigated, comprising the mixture according to the invention (product C) or the comparison systems (products A and B) are compared in Table 2a, below. The synergistic effect of the mixture according to the invention (product C) manifests itself here above all in the residual germ counts for *Aspergillus niger* after 7 days. As can be seen from the table, the germ count of *Aspergillus niger*, a germ which is particularly problematic in respect of preservation of industrial products, was reduced to cfu/ml at 7 days=6000 by using product C. In contrast, the active compound tested by means of product A in a dosage of 1.0 wt. % for comparison purposes (1,2-hexanediol+1,2-octanediol; amounts ratio 1:1; w/w) rendered possible no such significant reduction in the number of colony-forming units (cfu/ml at 7 days=302000), which also applies to product B in a dosage form of 1.0 wt. % (4-methylbenzyl alcohol of formula (II); cfu/ml at 7 days=167000). This test series thus shows by way of example that active compound mixtures of components (a) and (b) according to the invention have an action which is synergistically improved in comparison with product A (mixture comprising 1,2-hexanediol and 1,2-octanediol; ratio of amounts 1:1; w/w) and product B (4-methylbenzyl alcohol).

TABLE 2a

Testing for adequate preservation for product A, an active compound combination comprising 0.5% 1,2-hexanediol and 0.5% 1,2-octanediol in the amounts ratio of 1:1 (w/w), for product B comprising 1.0% of 4-methylbenzyl alcohol, (formula II) and for product C, the mixture according to the invention comprising 0.4% 1,2-hexanediol, 0.4% 1,2-octanediol and 0.2% 4-methylbenzylalcohol (formula II)

| Days | 1.0% product A (1,2-hexanediol plus 1,2-octanediol; 1:1 w/w) *Aspergillus niger* [cfu/ml] | 1.0% product B (4-methylbenzyl alcohol) *Aspergillus niger* [cfu/ml] | 1.0% product C (0.8% 1,2-hexanediol plus 1,2-octanediol; 1:1 w/w and 0.2% 4-methylbenzylalcohol) *Aspergillus niger* [cfu/ml] |
|---|---|---|---|
| 0 | 320000 | 320000 | 320000 |
| 2 | 284000 | 302000 | 302000 |
| 7 | 302000 | 167000 | 6000 |

Determination of Synergy Indices

TABLE 3a

Calculation of the synergy index (SI) at the time 7 days with the aid of the cfu/ml values for product A (0.5% 1,2-hexanediol and 0.5% 1,2-octanediol), product B (4-methylbenzyl alcohol; dosage: 1.0%) and product C (according to the invention); dosage of 1,2-hexanediol and 1,2-octanediol: each 0.4%; dosage of 4-methylbenzyl alcohol: 0.2%; test germ: *Aspergillus niger*

| | A 0.5% 1,2-hexanediol and 0.5% 1,2-octanediol | B 1.0% 4-methylbenzyl alcohol | C 0.4% 1,2-hexanediol and 0.4% 1,2-octanediol and 0.2% 4-methylbenzyl alcohol |
|---|---|---|---|
| *Aspergillus niger*: 7 days [cfu/ml] Kull's equation: SI = C × D/A + C × E/B | 302000 | 167000 | 6000 |
| A: Germ count for product A | 302000 | | |
| B: Germ count for product B | 167000 | | |

TABLE 3a-continued

Calculation of the synergy index (SI) at the time 7 days with the aid of the
cfu/ml values for product A (0.5% 1,2-hexanediol and 0.5% 1,2-octanediol),
product B (4-methylbenzyl alcohol; dosage: 1.0%) and product C (according to
the invention); dosage of 1,2-hexanediol and 1,2-octanediol: each 0.4%; dosage
of 4-methylbenzyl alcohol: 0.2%; test germ: *Aspergillus niger*)

|  | A<br>0.5% 1,2-<br>hexanediol and<br>0.5% 1,2-<br>octanediol | B<br>1.0% 4-<br>methylbenzyl<br>alcohol | C<br>0.4% 1,2-hexanediol and<br>0.4% 1,2-octanediol and<br>0.2% 4-methylbenzyl<br>alcohol |
|---|---|---|---|
| C: Germ count for product C | 6000 | | |
| D: Content of A in C | 0.8 | | |
| E: Content of B in C | 0.2 | | |
| SI: Synergy index | 0.023 | | |

Literature: Synergy index:
D. C. Steinberg; Cosmetics & Toiletries 115 (11); p. 59-62 (2000)
F. C. Kull et al.; Applied Microbiology 9; p. 538-541 (1961)

The calculation of the SI value for treatment of *Aspergillus niger* with product C (mixture of 1,2-hexanediol, 1,2-octanediol and 4-methylbenzyl alcohol) after an incubation phase of 7 days is shown above by way of example (Table 3a). The calculated SI of 0.023 clearly shows that the mixture is a highly synergistic combination of active compounds.

Outstanding results which confirm the superiority of product C according to the invention were likewise obtained in respect of the further test germs. In conclusion, efficient preservation is achieved because of an almost log 2 reduction achieved for mold (*Aspergillus niger*) and yeast (*Candida albicans*) after 7 days and an at least 3 log reduction for bacteria (*Pseudomonas aeruginosa, Staphylococcus aurues, Escherichia coli*) after 2 days.

Example 1b

Comparison of adequate preservation of cosmetic
formulations comprising a mixture of 1,2-hexanediol
and 1,2-octanediol (product A, not according to the
invention), 4-methylbenzyl alcohol (product B, not
according to the invention) and a mixture of 1,2-
hexanediol, 1,2-octanediol and 4-methylbenzyl alcohol (product C, according to the invention)

Testing for adequate preservation was carried out in accordance with the European Pharmacopoeia, as explained in Example 1a.

Test Germs:

The following microorganism strains were used for the tests for adequate preservation:

A: *Escherichia coli* ATCC 8739

B: *Pseudomonas aeruginosa* ATCC 9027

C: *Staphylococcus aureus* ATCC 6538

D: *Candida albicans* ATCC 10231

E: *Aspergillus niger* ATCC 16404

The initial germ count (cfu/ml; "0 value") was in the range of from 230000 to 400000 in the various test series.

Formulation:

For the tests for adequate preservation, a defined amount of the active compound combination according to the invention was incorporated into an O/W emulsion (product C). For comparison purposes, the comparison products were incorporated into separate O/W emulsions (products A and B).

Formulations with Products A, B and C:

TABLE 1b

|  | INCI name | Manufacturer | A<br>wt.-% | B<br>wt.-% | C (inventive)<br>wt.-% |
|---|---|---|---|---|---|
| Phase A | | | | | |
| Dracorin CE | Glyceryl Stearate Citrate | Symrise | 4.0 | 4.0 | 4.0 |
| PCL Solid | Stearyl Heptanoate,<br>Stearyl Caprylate | Symrise | 3.0 | 3.0 | 3.0 |
| Paraffin oil °E | Paraffinum Liquidum | Parafluid | 7.0 | 7.0 | 7.0 |
| Lanette 18 | Stearyl Alcohol | Cognis | 1.5 | 1.5 | 1.5 |
| Dracorin GMS | Glyceryl Stearate | Symrise | 1.5 | 1.5 | 1.5 |
| Dow Corning 200 fluid | Dimethicone | Dow Corning | 2.0 | 2.0 | 2.0 |
| Phase B | | | | | |
| Water, demineralized | Water (Aqua) | | to 100 | to 100 | to 100 |
| Carbopol ETD 2050 Polymer | Carbomer | Noveon | 0.15 | 0.15 | 0.15 |
| 1,2-Hexanediol | 1,2-Hexanediol | Symrise | 0.25 | — | 0.2 |
| 1,2-Octanediol | Caprylyl Glycol | Symrise | 0.75 | — | 0.6 |
| 4-Methylbenzyl alcohol | not INCI listed | Symrise | — | 1.0 | 0.2 |

TABLE 1b-continued

|  | INCI name | Manufacturer | A wt.-% | B wt.-% | C (inventive) wt.-% |
|---|---|---|---|---|---|
| Phase C |  |  |  |  |  |
| Neutralizer AMP-95 | Amino Methylpropanol | Dow/Angus | 0.1 | 0.1 | 0.1 |
| Total: |  |  | 100.0 | 100.0 | 100.0 | pH 5.5

Result:

The results of the preservative stress tests for *Aspergillus niger* for the active compound combinations investigated, comprising the mixture according to the invention (product C) or the comparison systems (products A and B) are compared in Table 2b. The synergistic effect of the mixture according to the invention (product C) manifests itself here above all in the residual germ counts for *Aspergillus niger* after 7 days. As can be seen from the table, it was possible to reduce the germ count of *Aspergillus niger*, a germ which is particularly problematic in respect of preservation of industrial products, to cfu/ml at 7 days=200 (which corresponds to an at least 3 log reduction) by using product C. In contrast, the active compound tested by means of product A in a dosage of 1.0 wt. % for comparison purposes (1,2-hexanediol+1,2-octanediol; amounts ratio 1:3; w/w) rendered possible no such significant reduction in the number of colony-forming units (cfu/ml at 7 days=207000), which also applies to product B in a dosage form of 1.0 wt. % (4-methylbenzyl alcohol of formula (II); cfu/ml at 7 days=167000). This test series thus shows by way of another example that active compound mixtures of components (a) and (b) according to the invention have an action which is synergistically improved in comparison with product A (mixture comprising 1,2-hexanediol and 1,2-octanediol; ratio of amounts 1:3; w/w) and product B (4-methylbenzyl alcohol).

TABLE 2b

Testing for adequate preservation for product A, an active compound combination comprising 0.25% 1,2-hexanediol, 0.75% 1,2-octanediol and for product B comprising 1.0% of 4-methylbenzyl alcohol, (formula II) and for product C, the mixture according to the invention comprising 0.2% 1,2-hexanediol, 0.6% 1,2-octanediol and 0.2% 4-methylbenzylalcohol (formula II)

| Days | 1.0% product A (1,2-hexanediol plus 1,2-octanediol; 1:3 w/w) *Aspergillus niger* [cfu/ml] | 1.0% product B (4-methylbenzyl alcohol) *Aspergillus niger* [cfu/ml] | 1.0% product C (0.2% 1,2-hexanediol and 0.6% 1,2-octanediol and 0.2% 4-methylbenzylalcohol) *Aspergillus niger* [cfu/ml] |
|---|---|---|---|
| 0 | 230000 | 320000 | 230000 |
| 2 | 110000 | 302000 | 59000 |
| 7 | 25000 | 167000 | 200 |

Determination of Synergy Indices

TABLE 3b

Calculation of the synergy index (SI) at the time 7 days with the aid of the cfu/ml values for product A (0.25% 1,2-hexanediol and 0.75% 1,2-octanediol), product B (4-methylbenzyl alcohol; dosage: 1.0%) and for product C (according to the invention; dosage of 1,2-hexanediol: 0.2%, dosage of 1,2-octanediol 0.6% and dosage of 4-methylbenzyl alcohol: 0.2%; test germ: *Aspergillus niger*)

|  | A 0.25% 1,2-hexanediol and 0.75% 1,2-octanediol | B 1.0% 4-methylbenzyl alcohol | C 0.2% 1,2-hexanediol and 0.6% 1,2-octanediol and 0.2% 4-methylbenzyl alcohol |
|---|---|---|---|
| *Aspergillus niger*: 7 days [cfu/ml] | 25000 | 167000 | 200 |
| Kull's equation: SI = C × D/A + C × E/B |  |  |  |
| A: Germ count for substance A | 25000 |  |  |
| B: Germ count for substance B | 167000 |  |  |
| C: Germ count for mixture A + B | 200 |  |  |
| D: Content of A in C | 0.8 |  |  |
| E: Content of B in C | 0.2 |  |  |
| SI: Synergy index | 0.007 |  |  |

Literature: Synergy index:
D. C. Steinberg; Cosmetics & Toiletries 115 (11); p. 59-62 (2000)
F. C. Kull et al.; Applied Microbiology 9; p. 538-541 (1961)

The calculation of the SI value for treatment of *Aspergillus niger* with product C (mixture of 1,2-hexanediol, 1,2-octanediol and 4-methylbenzyl alcohol) after an incubation phase of 7 days is shown above by way of example (Table 3b). The calculated SI of 0.007 clearly shows that the mixture is a highly synergistic combination of active compounds.

Outstanding results which confirm the superiority of product C according to the invention were likewise obtained in respect of the further test germs. In conclusion, efficient preservation is achieved because of an at least three log reduction achieved for mold (*Aspergillus niger*) and yeast (*Candida albicans*) after 7 days and an at least 3 log reduction for bacteria (*Pseudomonas aeruginosa, Staphylococcus aurues, Escherichia coli*) after 2 days.

Formulation:

For the tests for adequate preservation, a defined amount of the active compound combination according to the invention (product C) was incorporated into an O/W emulsion. For comparison purposes, the comparison products (product A and B) were incorporated into separate O/W emulsions.

Formulations with Products A, B and C:

TABLE 4

|  | INCI name | Manufacturer | A wt.-% | B wt.-% | C wt.-% |
|---|---|---|---|---|---|
| Phase A |  |  |  |  |  |
| Dracorin CE | Glyceryl Stearate Citrate | Symrise | 4.0 | 4.0 | 4.0 |
| PCL Solid | Stearyl Heptanoate, Stearyl Caprylate | Symrise | 3.0 | 3.0 | 3.0 |
| Paraffin oil °E | Paraffinum Liquidum | Parafluid | 7.0 | 7.0 | 7.0 |
| Lanette 18 | Stearyl Alcohol | Cognis | 1.5 | 1.5 | 1.5 |
| Dracorin GMS | Glyceryl Stearate | Symrise | 1.5 | 1.5 | 1.5 |
| Dow Corning 200 fluid | Dimethicone | Dow Corning | 2.0 | 2.0 | 2.0 |
| Phase B |  |  |  |  |  |
| Water, demineralised | Water (Aqua) |  | to 100 | to 100 | to 100 |
| Carbopol ETD 2050 Polymer | Carbomer | Noveon | 0.15 | 0.15 | 0.15 |
| 1,2-Octanediol | Caprylyl Glycol | Symrise | 1.0 | — | 0.8 |
| 4-Methylbenzyl alcohol | not INCI listed | Symrise | — | 1.0 | 0.2 |
| Phase C |  |  |  |  |  |
| Neutralizer AMP-95 | Amino Methylpropanol | Dow/Angus | 0.1 | 0.1 | 0.1 |
| Total: |  |  | 100.0 | 100.0 | 100.0 | pH 5.5

Example 2

Comparison of adequate preservation of cosmetic formulations comprising 1,2-octanediol (product A, not according to the invention), 4-methylbenzyl alcohol (product B, not according to the invention) and a mixture of 1,2-octanediol and 4-methylbenzyl alcohol (product C, according to the invention)

Testing for adequate preservation was carried out in accordance with the European Pharmacopoeia, as explained in Example 1a.

Test Germs:

The following microorganism strains were used for the tests for adequate preservation:
A: *Escherichia coli* ATCC 8739
B: *Pseudomonas aeruginosa* ATCC 9027
C: *Staphylococcus aureus* ATCC 6538
D: *Candida albicans* ATCC 10231
E: *Aspergillus niger* ATCC 16404

The initial germ count (CFU/g; "0 value") was in the range of from 230000 to 400000 in the various test series.

Result:

The results of the preservative stress tests for *Aspergillus niger* for the active compound combinations investigated, comprising the mixture according to the invention (product C) or the comparison systems (products A and B) are compared in Table 5. The synergistic effect of the mixture according to the invention (product C) manifests itself here above all in the residual germ counts for *Aspergillus niger* after 7 days. As can be seen from the table, it was possible to reduce the germ count of *Aspergillus niger*, a germ which is particularly problematic in respect of preservation of industrial products, to cfu/ml at 7 days=400 (which corresponds to an almost 3 log reduction) by using product C. In contrast, the active compound tested by means of product A in a dosage of 1.0 wt. % for comparison purposes (1,2-octanediol) rendered possible no such significant reduction in the number of colony-forming units (cfu/ml at 7 days=113000), which also applies to product B in a dosage form of 1.0 wt. % (4-Methylbenzyl alcohol of formula (II); cfu/ml at 7 days=167000). This test series thus shows again by way of example that active compound mixtures according to the invention have an action which is synergistically improved in comparison with product A (1,2-octanediol) and product B (4-methylbenzyl alcohol).

TABLE 5

Testing for adequate preservation for product A, an active compound combination comprising 1.0% of 1,2-octanediol, for product B comprising 1.0% of 4-methylbenzyl alcohol, (formula II) and for product C, the mixture according to the invention comprising 0.8% 1,2-octanediol and 0.2% 4-methylbenzyl alcohol (formula II)

| Days | 1.0% product A (1,2-octanediol) Aspergillus niger [cfu/ml] | 1.0% product B (4-methylbenzyl alcohol) Aspergillus niger [cfu/ml] | 1.0% product C (0.8% 1,2-octanediol; and 0.2% 4-methylbenzyl alcohol) Aspergillus niger [cfu/ml] |
|---|---|---|---|
| 0 | 320000 | 320000 | 320000 |
| 2 | 340000 | 302000 | 44000 |
| 7 | 113000 | 167000 | 400 |

Determination of Synergy Indices

TABLE 6

Calculation of the synergy index (SI) at the time 7 days with the aid of the cfu/ml values for product A (1,2-octanediol; dosage: 1%), product B (4-methylbenzyl alcohol; dosage: 1.0%) and for the synergistic mixture according to the invention (ratio of amounts of product A and product B: 0.8:0.2; w/w; dosage of 1,2-octanediol: 0.8%; dosage of 4-methylbenzyl alcohol: 0.2%); test germ: Aspergillus niger

| | A 1.0% 1,2-octanediol | B 1.0% 4-methylbenzyl alcohol | C 0.8% 1,2-octanediol and 0.2% 4-methylbenzyl alcohol |
|---|---|---|---|
| Aspergillus niger: 7 days [cfu/ml] | 113000 | 167000 | 400 |
| Kull's equation: SI = C × D/A + C × E/B | | | |
| A: Germ count for substance A | 113000 | | |
| B: Germ count for substance B | 167000 | | |
| C: Germ count for mixture A + B | 400 | | |
| D: Content of A in C | 0.8 | | |
| E: Content of B in C | 0.2 | | |
| SI: Synergy index | 0.003 | | |

Literature: Synergy index:
D. C. Steinberg; Cosmetics & Toiletries 115 (11); p. 59-62 (2000)
F. C. Kull et al.; Applied Microbiology 9; p. 538-541 (1961)

The calculation of the SI value for treatment of *Aspergillus niger* with product C (mixture of 1,2-octanediol and 4-methylbenzyl alcohol) after an incubation phase of 7 days is shown above by way of example (Table 6). The calculated SI of 0.003 clearly shows that the mixture is a highly synergistic combination of active compounds.

Outstanding results which confirm the superiority of product C according to the invention were likewise obtained in respect of the further test germs. In conclusion, efficient preservation is achieved because of a nearly three log reduction achieved for mold (*Aspergillus niger*) and yeast (*Candida albicans*) after 7 days and an at least 3 log reduction for bacteria (*Pseudomonas aeruginosa, Staphylococcus aurues, Escherichia coli*) after 2 days.

Example 3

Comparison of adequate preservation of cosmetic formulations comprising 1,2-pentanediol, 1,2-hexanediol or 1,2-decanediol (not according to the invention), 4-methylbenzyl alcohol (not according to the invention) and mixtures of 1,2-pentanediol and 4-methylbenzyl alcohol (according to the invention), 1,2-hexanediol and 4-methylbenzyl alcohol (according to the invention) or 1,2-decanediol and 4-methylbenzyl alcohol (according to the invention)

TABLE 7

Calculation of the synergy indices (SI) at the time 7 days and 14 days with the aid of the cfu/ml values for 1,2-pentanediol (dosage: 4.0%), 4-methylbenzyl alcohol (dosage: 0.4%) and for the synergistic mixture according to the invention (50% of amount of 1,2-pentanediol; dosage 2.0% and 50% of amount of 4-methylbenzylalcohol; dosage: 0.2%) test germ: Aspergillus niger

| | | cfu/ml at 0 days | cfu/ml at 2 days | cfu/ml at 7 days | cfu/ml at 14 days |
|---|---|---|---|---|---|
| 1,2-Pentanediol (4%) | Aspergillus niger | 250000 | 246000 | 265000 | 246000 |

TABLE 7-continued

Calculation of the synergy indices (SI) at the time 7 days and
14 days with the aid of the cfu/ml values for 1,2-pentanediol
(dosage: 4.0%), 4-methylbenzyl alcohol (dosage: 0.4%) and for
the synergistic mixture according to the invention (50% of amount
of 1,2-pentanediol; dosage 2.0% and 50% of amount of 4-methylbenzylalcohol;
dosage: 0.2%) test germ: *Aspergillus niger*

|  |  | cfu/ml at 0 days | cfu/ml at 2 days | cfu/ml at 7 days | cfu/ml at 14 days |
|---|---|---|---|---|---|
| 4-Methylbenzyl alcohol (0.4%) | *Aspergillus niger* | 250000 | 208000 | 302000 | 132000 |
| 1,2-Pentanediol (2%) and 4-Methylbenzyl alcohol (0.2%) | *Aspergillus niger* | 250000 | 246000 | 321000 | 59000 |

SI = 0.3430

The calculation of the SI values for treatment of *Aspergillus niger* with a mixture of 1,2-pentanediol (2%) and 4-methylbenzyl alcohol (0.2%) after an incubation phase of 7 days and 14 days is shown above by way of example (Table 7). In the early stage at day 7 no synergism could be observed most probably because of the weaker antimicrobial activity of 1,2-pentanediol compared to 1,2-hexanediol, 1,2-octanediol or 1,2-decanediol. However, the calculated SI value of 0.3430 at day 14 clearly shows that even a mixture comprising 1,2-pentanediol (with only moderate antimicrobial activity against *Aspergillus niger*) and 4-methylbenzyl alcohol is a synergistic combination of active compounds.

Further combinations comprising either 1,2-hexanediol and 4-methylbenzl alcohol or 1,2-decanediol and 4-methylbenzyl alcohol showed a synergistic activity already after a 7 days incubation period as shown in the following tables 8 and 9

TABLE 8

Calculation of the synergy indices (SI) at the time 7 days with
the aid of the cfu/ml values for 1,2-hexanediol (dosage: 3.0%),
4-methylbenzyl alcohol (dosage: 0.4%) and for the synergistic
mixture according to the invention (50% of amount of 1,2-pentanediol;
dosage 1.5% and 50% of amount of 4-methylbenzylalcohol; dosage:
0.2%) test germ: *Aspergillus niger*

|  |  | cfu/ml at 0 days | cfu/ml at 2 days | cfu/ml at 7 days |
|---|---|---|---|---|
| 1,2-Hexanediol (3.0%) | *Aspergillus niger* | 250000 | 212000 | 132000 |
| 4-Methylbenzyl alcohol (0.4%) | *Aspergillus niger* | 250000 | 208000 | 302000 |
| 1,2-Hexanediol (1.5%) and 4-Methylbenzyl alcohol (0.2%) | *Aspergillus niger* | 250000 | 208000 | 13000 |

SI = 0.0707

The calculation of the SI value for treatment of *Aspergillus niger* with a mixture of 1,2-hexanediol and 4-methylbenzyl alcohol after an incubation phase of only 7 days is shown above by way of example (Table 8). The calculated SI value of 0.0707 at day 7 clearly shows that a mixture comprising 1,2-hexanediol and 4-methylbenzyl alcohol is a highly synergistic combination of active compounds.

TABLE 9

Calculation of the synergy indices (SI) at the time 7 days with
the aid of the cfu/ml values for 1,2-decanediol (dosage: 1.0%),
4-methylbenzyl alcohol (dosage: 0.4%) and for the synergistic
mixture according to the invention (50% of amount of 1,2-pentanediol;
dosage 0.5% and 50% of amount of 4-methylbenzylalcohol; dosage:
0.2%) test germ: *Aspergillus niger*

|  |  | cfu/ml at 0 days | cfu/ml at 2 days | cfu/ml at 7 days |
|---|---|---|---|---|
| 1,2-Decanediol (1.0%) | *Aspergillus niger* | 250000 | 208000 | 302000 |
| 4-Methylbenzyl alcohol (0.4%) | *Aspergillus niger* | 250000 | 208000 | 302000 |
| 1,2-Decanediol (1.5%) and 4-Methylbenzyl alcohol (0.2%) | *Aspergillus niger* | 250000 | 208000 | 24000 |

SI = 0.0794

The calculation of the SI value for treatment of *Aspergillus niger* with a mixture of 1,2-decanediol and 4-methylbenzyl alcohol after an incubation phase of only 7 days is shown above by way of example (Table 9). The calculated SI value of 0.0794 at day 7 clearly shows that a mixture comprising 1,2-decanediol and 4-methylbenzyl alcohol is also a highly synergistic combination of active compounds.

Example 4

Comparison of adequate preservation of cosmetic formulations with a high amount of organic UV filters and having a SPF of equal or greater than 15 comprising either Phenonip® (product A2; not according to the invention) or a mixture consisting of 1,2-octanediol and 4-methylbenzyl alcohol (product "C8-4MBA" according to the invention)

Testing for Adequate Preservation Against Germs in Sunscreen Formulations:

For the tests for adequate preservation, 1 wt.-% of the respective active compounds were incorporated into separate O/W emulsions: A2 is the comparison formulation comprising Phenonip® (not according to the present invention). Phenonip® is a commercially available (Clariant, Nipa preservatives) and in cosmetic formulations widely used antimicrobial active mixture consisting of phenoxyethanol, methylparaben, ethylparaben, butylparaben, propylparaben and isobutylparaben.

"C8-4MBA" is a composition according to the present invention comprising 0.50 wt.-% 1,2-octanediol and 0.5 wt.-% 4-methylbenzyl alcohol.

TABLE 10

| Trade Name | INCI | A2 | C8-4MBA |
|---|---|---|---|
| Emulsiphos | Potassium cetyl phosphate, hydrogenated palm glycerides | 2.00 | 2.00 |
| PCL Solid | Stearyl heptanoate, stearyl caprylate | 2.00 | 2.00 |
| Lanette 16 | Cetyl alcohol | 1.50 | 1.50 |
| Dragoxat 89 | Ethylhexyl ethylisononanoate | 2.00 | 2.00 |
| Neutral Oil | Caprylic/capric triglyceride | 3.00 | 3.00 |
| Tegosoft TN | C12-15 Alkyl benzoate | 3.00 | 3.00 |
| Neo Heliopan BB | Benzophenone-3 | 6.00 | 6.00 |
| Neo Heliopan HMS | Homosalate | 10.00 | 10.00 |
| Neo Heliopan OS | Ethylhexyl salicylate | 5.00 | 5.00 |
| Neo Heliopan 357 | Butyl methoxy dibenzoyl-methane | 3.00 | 3.00 |
| Neo Heliopan AV | Ethylhexyl methoxycinnamate | 7.50 | 7.50 |
| Carbopol ETD 2050 | Carbomer | 0.20 | 0.20 |
| Keltrol T | Xanthan gum | 0.20 | 0.20 |
| Water | Water (Aqua) | 50.45 | 50.45 |
| Glycerol | Glycerine | 3.00 | 3.00 |
| AMP | 2-Amino-2-methyl-1-propanol | 0.15 | 0.15 |
| Phenonip ® | Phenoxyethanol (and) Methylparaben (and) Butylparaben (and) Ethylparaben (and) Propylparaben | 1.00 | — |
| "C8-4MBA" 1,2-Octanediol, 4-methylbenzyl alcohol | Caprylyl Glycol, 4-methylbenzyl alcohol (not INCI listed) | — | 1.00 |

Testing for adequate preservation was carried out in accordance with the European Pharmacopoeia, as explained in Example 1a.

The initial germ count (cfu/ml; "0 value") was in the range of from 200,000 to 400,000 in the various test series.

Result:

Preservation Test for *Candida Albicans* Using Strain *Candida Albicans* ATCC 10231

| Days | A2 (Phenonip ®) [cfu/ml] | C8-4MBA [cfu/ml] |
|---|---|---|
| 0 | 400,000 | 280,000 |
| 2 | 194,000 | <100 |
| 7 | 157,000 | 0 |
| 14 | 157,000 | 0 |

Preservation Test for *Aspergillus Niger* Using Strain *Aspergillus Niger* ATCC 16404

| Days | A2 (Phenonip ®) [cfu/ml] | C8-4MBA [cfu/ml] |
|---|---|---|
| 0 | 230,000 | 250,000 |
| 2 | 189,000 | 170,000 |
| 7 | 93,000 | 3600 |
| 14 | 3,000 | 0 |

Outstanding results which confirm the superiority of C8-4MBA according to the invention were likewise obtained in respect to further test germs (*Pseudomonas aeruginosa, Staphylococcus aurues, Escherichia coli*).

In conclusion, efficient preservation with mixtures according to the invention is even achieved for very difficult to preserve cosmetic formulations with a high amount of organic UV filters and having a SPF of equal or greater than 15. An at least 3 log reduction was achieved for yeast (*Candida albicans*) and an almost 2 log reduction was achieved for mold (*Aspergillus niger*) after 7 days. An at least 3 log reduction was also achieved for bacteria (*Pseudomonas aeruginosa, Staphylococcus aureus, Escherichia coli*) after 2 days.

Example P1

Free Perfume Oil (not According to the Present Invention)

| Components | Perfume oil P1 parts by weight |
|---|---|
| 10-undecenal, 10% in DPG | 2.00 |
| Vertocitral (2,4-dimethyl-3-cyclohexencarboxaldehyde) | 0.50 |
| cis-3-Hexenyl acetate, 10% in DPG | 7.50 |
| Allyl amyl glycolate | 2.00 |
| Melonal (2,6-dimethyl-5-hepten-1-al) | 0.50 |
| Bergamot oil | 70.00 |
| Dihydromyrcenol | 80.00 |
| Cyclogalbanate (allylcyclohexyloxy acetate) | 20.00 |
| Terpinyl acetate | 40.00 |
| *Litsea cubeba* oil | 2.00 |
| Lemon oil | 50.00 |
| Orange oil | 20.00 |
| Grapefruit oil | 10.00 |
| Lavandin oil abrialis | 10.00 |
| Isobornyl acetate | 3.00 |
| Lilial (2-methyl-3-(4-tert-butyl-phenyl)propanal) | 10.00 |
| Calone ® 1951 (7-methyl-2H-1,5-benzodioxepin-3(4H)-one) | 2.50 |
| Florhydral ® (3-(3-isopropylphenyl)butanal) | 1.50 |
| Florol ® (2-isobutyl-4-methyltetrahydro-2H-pyran-4-ol) | 12.00 |
| Tetrahydrolinalool | 75.00 |
| *Geranium* oil | 5.00 |
| Isodamascon (1-(2,4,4-trimethyl-2-cyclohexen-1-yl)-2-buten-1-one), 10% in DPG | 2.00 |
| Resedafol, 10% in DPG [2-(1-propoxyethoxy)ethyl]benzol | 1.00 |
| Methyl dihydrojasmonate (Hedione ® HC) | 158.00 |
| L-menthylmethylether | 50.00 |
| Jessemal (3-butyl-5-methyl tetrahydropyran-4-yl-acetate) | 4.00 |
| Benzyl salicylate | 10.00 |
| Anethole | 3.00 |
| Methylcedrylketone | 50.00 |
| Iso E Super ® [++] | 25.00 |
| Ambrocenide ® ((4aR,5R,7aS,9R)-octahydro-2,2,5,8,9,9a-hexamethyl-4H-4a,9-methanoazuleno(5,6-d)-1,3-dioxol), 1% in DPG | 3.00 |
| Timberol(1-(2,2,6-trimethylcyclohexyl)hexan-3-ol) | 2.00 |
| Patchouli oil | 3.50 |
| Evernyl ® (methyl-2,4-dihydroxy-3,6-dimethylbenzoate) | 1.50 |
| Labdanum absolute, 20% in DPG | 2.00 |
| Amber Core (1-[[2-(1,1-dimethylethyl)cyclohexyl]oxy]-2-butanol) | 10.00 |
| Ambraketal (dodecahydro-3,8,8,11a-tetramethyl-5H-3,5a-epoxynaphth[2,1-c]oxepin) | 1.50 |
| Hydroxyambran ® (2-cyclododecylpropanol), 50% in DPG | 5.00 |
| Macrolide ® (15-cyclopentadecanolide) | 35.00 |
| Globalide ® (15-pentadec-(11/12)-enolide) | 20.00 |
| Globanone ® ((E/Z)-8-cyclohexadecenone) | 20.00 |
| Isopropylmyristate | 170.00 |
| TOTAL: | 1,000.00 |

[++] Octahydro-2,3,8,8-tetramethyl-2-acetonaphthone and 2-acetyl-1,2,3,4,6,7,8-octahydro-2,3,8,8-tetramethylnaphthaline

Example P2

Free Perfume Oil with Rose Odor (not According to the Present Invention)

| Components | Perfume oil P2 parts by weight |
|---|---|
| Acetophenone, 10% in DPG | 10.00 |
| n-Undecanal | 5.00 |
| Aldehyde C14 so-called (peach aldehyde) | 15.00 |
| Allyl amyl glycolate, 10% in DPG | 20.00 |
| Amyl salicylate | 25.00 |
| Benzyl acetate | 60.00 |
| Citronellol | 80.00 |
| d-Limonen | 50.00 |
| Trans-9 decenol | 15.00 |
| Dihydromyrcenol | 50.00 |
| Dimethylbenzyl carbinyl acetate | 30.00 |
| Diphenyl oxide | 5.00 |
| *Eucalyptus* oil | 10.00 |
| Geraniol | 40.00 |
| Nerol | 20.00 |
| *Geranium* oil | 15.00 |
| Hexenol cis-3, 10% in DPG | 5.00 |
| Hexenyl salicylate cis-3 | 20.00 |
| Indol, 10% in DPG | 10.00 |
| Alpha-Ionone | 15.00 |
| Beta-Ionone | 5.00 |
| Lilial (2-methyl-3-(4-tert-butyl-phenyl)propanal) | 60.00 |
| Linalool | 40.00 |
| Methylphenyl acetate | 10.00 |
| Phenylethyl alcohol | 275.00 |
| Styrene acetate | 20.00 |
| Terpineol | 30.00 |
| Tetrahydrolinalool | 50.00 |
| Cinnamic alcohol | 10.00 |
| TOTAL: | 1,000.00 |

Formulation F1: Sunscreen Lotion (According to the Present Invention)

| Raw Material | % weight |
|---|---|
| Phase 1 | |
| Potassium Cetyl Phosphate, Hydrogenated Palm Glycerides | 1.00 |
| alpha-Bisabolol | 0.10 |
| Cetearyl Alcohol | 1.50 |
| Myristyl Myristate | 1.00 |
| Cetearyl Ethylhexanoate | 4.00 |
| Stearyl Heptanoate, Stearyl Caprylate | 1.00 |
| Cyclopentasiloxane, Cyclohexasiloxane | 0.50 |
| Butyl Methoxydibenzoylmethane (avobenzone) | 1.50 |
| 4-methylbenzylidene Camphor | 1.50 |
| Ethylhexyl Methoxycinnamate (Neo Heliopan ®AV) | 8.00 |
| VP/Hexadecene Copolymer | 1.00 |
| Acrylates/C10-30 Alkyl Acrylate Crosspolymer | 0.10 |
| Phase 2 | |
| Water | Ad 100 |
| Pentylene Glycol (1,2-Pentanediol) | 2.00 |
| Caprylyl Glycol (1,2-Octanediol) | 0.50 |
| Phase 3 | |
| Sodium Hydroxide, 10% solution | 0.50 |
| Phase 4 | |
| Fragrance of Example P1 | 0.20 |
| Phase 5 | |
| 4-Methylbenzyl alcohol of formula (II) | 0.50 |

Formulation F2: Silicone Emulsion (According to the Present Invention)

| Raw Material | % weight |
|---|---|
| Phase 1 | |
| Potassium Cetyl Phosphate, Hydrogenated Palm Glycerides | 1.00 |
| Cyclohexasiloxane | 4.00 |
| Cetearyl Alcohol | 1.50 |
| Phenyl Trimethicone | 3.00 |
| Stearyl Heptanoate, Stearyl Caprylate | 3.00 |
| Dimethicone | 1.00 |
| Xanthan Gum | 0.20 |
| Isoamyl p-Methoxycinnamate | 5.00 |
| p-Methoxycinnamic acid-2-ethylhexyl ester (Neo Heliopan ®AV) | 5.00 |
| Butyl Methoxydibenzoylmethane (avobenzone) | 0.50 |
| Phase 2 | |
| Water | Ad 100 |
| 1,2-Hexanediol | 0.40 |
| Caprylyl Glycol (1,2-Octanediol) | 0.40 |
| Phase 3 | |
| 4-Methylbenzyl alcohol of formula (II) | 0.20 |
| Fragrance Example P2 | 0.25 |

Formulation F3: W/O Sunscreen Lotion (According to the Present Invention)

| Raw Material | % weight |
|---|---|
| Phase 1 | |
| Polyglyceryl-2 Dipolyhydroxystearate | 3.00 |
| Glyceryl Oleate | 1.00 |
| Beeswax | 1.20 |
| Ethylhexyl Isononanoate | 2.00 |
| Caprylic/Capric Triglyceride | 3.00 |
| C 12-15 Alkyl Benzoate | 3.00 |
| Benzophenone-3 | 6.00 |
| Homosalate | 10.00 |
| Ethylhexyl Salicylate | 5.00 |
| Butyl Methoxydibenzoylmethane (avobenzone) | 3.00 |
| Ethylhexyl Methoxycinnamate | 7.50 |
| Phase 2 | |
| Water | Ad 100 |
| Caprylyl Glycol (1,2-Octanediol) | 0.50 |
| Phase 3 | |
| Magnesium Sulfate | 0.70 |
| Phase 4 | |
| Sodium Chloride | 0.50 |
| Phase 5 | |
| 4-Methylbenzyl alcohol of formula (II) | 0.50 |
| Fragrance of Example P2 | 0.50 |

Formulation F4-F13: Cosmetic formulations comprising a sufficient antimicrobial active amount of
4-methylbenzyl alcohol of formula II
and/or
at least one 1,2-alkanediol.
and/or
at least one further antimicrobial selected from
  (ii) benzoic acid (INCI: Benzoic Acid) and its esters and salts,
  (iii) 4-hydroxybenzoic acid and its esters (INCI: Parabenes) and salts,
  (iv) 2,4-hexadienoic acid (INCI: Sorbic Acid) and its salts,
  (v) 2-phenoxyethanol (INCI: Phenoxyethanol)

(vi) 3-iodo-2-propinyl-butylcarbamate (INCI: Iodopropynyl Butylcarbamate),
(vii) 3-(4-chlorphenoxy)-1,2-propane-1,2-diol (INCI: Chlorphenesin),
(viii) urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxymethylurea (INCI: Diazolidinyl Urea) and N-(4-chlorophenyl)-N'-(3,4-dichlorophenyl)-urea (INCI: Triclocarban),
(ix) 1,3-bis-(hydroxymethyl)-5,5-dimethyl-2,4-imidazolidindione (INCI: DMDM hydantoin),
(x) 1,2-propanediol, 3-(2-ethylhexyloxy) (INCI: Octoxyglycerin),
(xi) isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone)

with formulations 4-13 having the following meaning
4=skin lightening day cream O/W
5=skin soothing lotion with plant extracts O/W
6=after sun balm
7=body spray
8=broad band sun protection lotion (O/W),
9=W/O night cream
10=shampoo
11=self tanning cream
12=barriere repair cream O/W
13=antiperspirant//deodorant roll-on

| RAW MATERIAL-NAME (PRODUCER) | INCI | FORMULATION | | | | | | | | | |
|---|---|---|---|---|---|---|---|---|---|---|---|
| | | 4 | 5 | 6 | 7 | 8 | 9 | 10 | 11 | 12 | 13 |
| 4-Methylbenzylalcohol (formula II) | INCI | 0.2 | 0.2 | 0.2 | 0.1 | 0.4 | 0.2 | 0.05 | 0.2 | 1.0 | 0.1 |
| 1,2-Pentanediol (Symrise) | Pentylene Gylcol | | | 1.0 | 1.0 | | 1.0 | 2.0 | | | |
| 1,2-Hexanediol (Symrise) | 1,2-Hexanediol | 0.2 | 0.4 | 0.2 | 0.1 | 0.4 | 0.4 | | 1.0 | | |
| 1,2-Octanediol (Symrise) | Caprylyl Glycol | 0.6 | 0.4 | 0.6 | 0.3 | 1.2 | 0.4 | | | 0.6 | |
| 1,2-Decanediol (Symrise) | Decylene Glycol | | | | | 0.2 | | | | | 0.3 |
| Abil 350 (Degussa-Goldschmidt) | Dimethicone | 0.5 | 2.0 | 1.0 | | | | | 0.5 | 0.5 | |
| Allantoin (Merck) | Allantoin | | 0.2 | 0.1 | | | | | | | |
| Aloe Vera Gel Concentrate 10/1 (Symrise) | Water (Aqua), Aloe Barbadensis Leaf Juice | | | 3.0 | | | 3.0 | | | | |
| Alugel 34 TH (Baerlocher) | Aluminium Stearate | | | | | | | | 1.0 | | |
| Aqua-Ceramide (Kao) | Cetyloxypropyl Glyceryl Methoxypropyl Myristamide | | 0.1 | | | | | | | | 0.1 |
| Arbutin (Sabinsa) | β-Arbutin | 1.0 | | | | | | | | | |
| Sodium Ascorbyl Phosphate (EMD Chemicals) | Sodium Ascorbyl Phosphate | 2.0 | 1.0 | | | | | | | | |
| -(-Alpha-)-Bisabolol, natural (Symrise) | Bisabolol | 0.3 | 0.4 | | | | | 0.05 | | 0.5 | |
| Benzoic Acid, 4-hydroxy-, methylester | Methylparaben | | | | | | | 0.3 | | | |
| Benzoic Acid, 4-hydroxy-, ethylester | Ethylparaben | | | | | | | 0.1 | | | |
| Benzoic Acid, 4-hydroxy-, butylester | Propylparaben | | | | | | | 0.1 | | | |
| Benzoic Acid, 4-hydroxy-, isobutylester | Butylparaben | | | | | | | 0.1 | | | |
| 1,3-bis-(hydroxymethyl)-5,5-dimethyl-2,4-imidazolidindione | DMDM hydantoin | | | | | | | | | 0.5 | |
| Butylene Glycol | Butylene Glycol | | | | | 5.0 | | | | | |
| Carbopol ETD | Carbomer | | | | | | 0.2 | | | | |

-continued

| RAW MATERIAL-NAME (PRODUCER) | | FORMULATION | | | | | | | | | |
|---|---|---|---|---|---|---|---|---|---|---|---|
| | | 4 | 5 | 6 | 7 | 8 | 9 | 10 | 11 | 12 | 13 |
| 2050 (Noveon) Carbopol | Carbomer | | 0.1 | | | | | | | | |
| Ultrez-10 (Noveon) | | | | | | | | | | | |
| Ceramide 2 (Sederma) | Ceramide 2 | 0.1 | | | | | | | | | |
| Ceramide PC104 (Pacific Corporation) | Hydroxypropyl Bispalmitamide MEA | | | | | | 0.1 | | | | |
| Ceramide SL (Sino Lion) | Hydroxyethyl Palmityl Oxyhydroxypropyl Palmitamide | | | | | | | 0.1 | | | |
| Cetiol OE (Cognis) | Dicaprylyl Ether | | | 4.0 | | | | | | | |
| Cetiol SB 45 (Cognis) | *Butyrospermum Parkii* (Shea Butter) | | | | | 1.0 | | | | | |
| 5-chloro-2-methyl-3(2H)-isothiazolinone | Methylchloroisothiazolinone | | | | | | | | | 0.0003 | |
| Citric Acid 10% sol. | Citric Acid | | | | | | | 0.3 | | | |
| Comperlan 100 (Cognis) | Cocamide MEA | | | | | | | 0.5 | | | |
| Dihydroxyacetone (Merck) | Dihydroxyacetone | | | | | | | | | 5.0 | |
| Dow Corning 246 Fluid (Dow Corning) | Cyclohexasiloxane and Cyclopentasiloxane | | | | | | 2.0 | | | | |
| Dow Corning 345 Fluid (Dow Corning) | Cyclomethicone | | | | 0.5 | | | | | | |
| D-Panthenol (BASF) | Panthenol | | | 1.0 | | | | | | | |
| Dracorin CE (Symrise) | Glyceryl Stearate Citrate | 5.0 | | | | | | | 5.0 | 1.5 | |
| Dracorin GMS (Symrise) | Glyceryl Stearate | | 2.0 | | | | | | | 2.0 | |
| Dracorin GOC (Symrise) | Glyceryl Oleate Citrate, Caprylic/Capric Triglyceride | | | | | 2.0 | | | | | |
| Drago-Beta-Glucan (Symrise) | Water (Aqua), Butylene Glycol, Glycerin, *Avena Sativa* (Oat), Kernel Extract | 0.3 | | | | | | | | | |
| Dragocid Liquid (Symrise) | Phenoxyethanol, Methylparaben, Ethylparaben, Butylparaben, Propylparaben, Isobutylparaben | | 0.8 | 0.7 | | 0.7 | 0.8 | | | 0.8 | |
| Dragoderm (Symrise) | Glycerin, *Triticum Vulgare* (Wheat) Gluten, Water (Aqua) | | | | | | | | 2.0 | | |
| Drago-Oat-Active (Symrise) | Water (Aqua), Butylene Gylcol, *Avena Sativa* (Oat) Kernel Extract | | | | 1.0 | | | | | | |
| Dragosan W/O Liquid (Symrise) | Polyglyceryl-3-Polyricinoleate, Sorbitan Isostearate | | | | | | | 1.0 | | | |
| Dragosan W/O P (Symrise) | Sorbitan Isostearate, Hydrogenated Castor Oil, Ceresin, Beeswax (Cera Alba) | | | | | | | 6.0 | | | |
| Dragoxat EH (Symrise) | Ethylhexy Ethylhexanoate | 3.0 | 3.0 | | 4.0 | | | | 3.0 | | |

-continued

| RAW MATERIAL-NAME (PRODUCER) | | FORMULATION | | | | | | | | | |
|---|---|---|---|---|---|---|---|---|---|---|---|
| | | 4 | 5 | 6 | 7 | 8 | 9 | 10 | 11 | 12 | 13 |
| Dragoxat 89 (Symrise) | Ethylhexyl Ethylisononanoate | | | | | | | | | 2.0 | |
| EDETA B Pulver (BASF) | Tetrasodium EDTA | | | | | | | 0.1 | | | |
| EDETA DB (BASF) | Disodium EDTA | | | | | 0.1 | | | 0.1 | | |
| Emulsiphos (Symrise) | Potassium Cetyl Phosphate, Hydrogenated Palm Glycerides | | 2.0 | | | 1.5 | | | | 2.0 | |
| Ethanol 96% | Ethanol | | | | | | | | 2.0 | | 30.0 |
| Extrapone Green Tea GW (Symrise) | Glycerin, Water (Aqua), *Camellia Sinensis* Leaf Extract | | 0.2 | | | | | | | | |
| Extrapone Witch Hazel Distillate colorless (Symrise) | Propylene Glycol, *Hamamelis Virginiana* (Witch Hazel) Water, Water (Aqua), *Hamamelis Virginiana* (Witch Hazel) Extract | | | | | | | 1.0 | | | |
| Extrapone Rosemary GW (Symrise) | Glycerin, Water (Aqua), *Rosmarinus officinalis* (Rosemary) Leaf Extract | | 0.3 | | | | | | | 0.5 | |
| Farnesol (Symrise) | Farnesol | | | | | | | | | | 0.5 |
| Frescolat ML crist. (Symrise) | Menthyl Lactate | | | 0.8 | | | | | | | |
| Genapol LRO liquid (Cognis) | Sodium Laureth Sulfate | | | | | | | 37.0 | | | |
| Givobio GZN (Seppic) | Zinc Gluconate | | | | | | | | | 0.5 | |
| Glycerin 85% | Glycerin | 3.0 | 2.0 | 4.0 | | 4.7 | 2.0 | | 1.5 | 3.0 | |
| Hydroviton (Symrise) | Water, Glycerin, Sodium Lactate, TEA Lactate, Serine, Lactic Acid, Urea, Sorbitol, Sodium Chloride, Lauryl Diethylenediamino glycine, Lauryl Aminopropylglycine, Allantoin | | | | | | | | | 1.0 | |
| Ingwer $CO_2$ Extrakt (Flavex) | *Zingiber Officinale* (Ginger) Root Extract | 0.003 | | | | | | | | 0.01 | 0.001 |
| Irgasan DP 300 (Ciba Geigy) | Triclosan | | | | | | | | | | 0.3 |
| Isodragol (Symrise) | Triisononanoin | | 2.0 | | | | | | | 3.0 | |
| Isopropylpalmitate (Symrise) | Isopropyl Palmitate | 4.0 | | | | | | | 4.0 | | |
| Karion F (Merck) | Sorbitol | | | | | | | 2.0 | | | |
| Keltrol RD (CP-Kelco) | Xanthan Gum | 0.2 | 0.1 | | | | | | | | |
| Keltrol T (Danby-Chemie) | Xanthan Gum | | | | | 0.2 | | | 0.3 | | |
| Kojic acid (Cosmetochem) | Kojoc acid | 1.0 | | | | | | | | | |
| Lanette 16 (Cognis) | Cetyl Alcohol | 1.0 | | | | | | | 1.0 | | |
| Lanette O (Cognis) | Cetearyl Alcohol | | 3.0 | | | 1.0 | | | | 2.0 | |
| Lara Care A-200 (Rahn) | Galactoarabinan | | | 0.3 | | | | | | | |

-continued

| RAW MATERIAL-NAME (PRODUCER) | | FORMULATION | | | | | | | | | |
|---|---|---|---|---|---|---|---|---|---|---|---|
| | | 4 | 5 | 6 | 7 | 8 | 9 | 10 | 11 | 12 | 13 |
| Magnesium Chloride (Merck) | Magnesium Chloride | | | | | | 0.7 | | | | |
| 2-methyl-3(2H)-isothiazolinone | Methylisothiazolinone | | | | | | | | | 0.0001 | |
| Merquat 550 (Ondeo Nalco) | Polyquaternium-7 | | | | | | | 0.5 | | | |
| NaOH 10% sol. | Sodium Hydroxide | | | | | | | | | 0.3 | |
| Naringin (Exquim) | 4′,5,7-Trihydroxyflavon-7-O-neohesperidosid | | | | | | | 0.5 | 2.0 | | |
| Sodium benzoate | Sodium Benzoate | | | | | | | | | | 0.5 |
| Natrosol 250 HHR (Aqualon) | Hydroxyethylcellulose | | | | | | | | | | 0.3 |
| Neo Heliopan 357 (Symrise) | Butyl Methoxy-dibenzoylmethane | | | | | 1.0 | | | | | |
| Neo Heliopan AP (Symrise) (10% as Na-salt) | Disodium Phenyl Dibenzimidazole Tetrasulfonate | | | | | 10 | | | | | |
| Neo Heliopan AV (Symrise) | Ethylhexyl Methoxycinnamate | | | | | 3.0 | | | | | |
| Neo Heliopan Hydro (Symrise) (15% as Na-salt) | Phenylbenzimidazole Sulfonic Acid | | | | | 6.7 | | | | | |
| Neo Heliopan MBC (Symrise) | 4-Methylbenzylidene Camphor | | | | | 1.5 | | | | | |
| Neo Heliopan OS (Symrise) | Ethylhexyl Salicylate | | | | | 5.0 | | | | | |
| Neutral Oil | Caprylic/Capric Triglyceride | 6.0 | | | 4.0 | 2.0 | | | 6.0 | 10.0 | |
| Oxynex 2004 (Merck) | BHT | | | | | | 0.1 | | | | |
| Paraffinöl 5 Grad E (Parafluid) | *Paraffinum Liquidum* | | | | | 4.0 | | | | | |
| PCL Liquid 100 (Symrise) | Cetearyl Ethyl-hexoate | 3.0 | 5.0 | | 7.0 | | | | | | |
| PCL Solid (Symrise) | Stearyl Heptanoate, Stearyl Caprylate | | 2.0 | | | | | | | | |
| PCL-Liquid (Symrise) | Cetearyl Ethyl-hexanoate, Isopropyl Myristate | | | | | | | 12.0 | | 3.0 | |
| Pemulen TR-2 (Noveon) | Acrylates/C10-30 Alkyl Acrylate Crosspolymer | | | 0.3 | 0.2 | | | | | | |
| 4-(1-Phenylethyl)1,3-benzenediol | 4-(1-Phenylethyl)1,3-benzenediol | 0.5 | | | | | | | | | |
| Propylene Glycol-1,2 | Propylene Glycol | | 5.0 | | | | | | | | |
| Pseudoceramide 391 | N-(1-Hexadecanoyl)-4-hydroxy-L-prolin-(1-hexadecyl-ester | | 0.1 | | | | | 0.2 | | 0.5 | |
| Retinyl Palmitate in Oil (DSM Nutrional Products) | Retinyl Palmitate | | | | | | 0.2 | | | | |
| Sepigel 305 | Polyacrylamide, C13-14 Isoparaffin, Laureth-7 | | | | | | | | 1.0 | | |
| Sodium Chloride | Sodium Chloride | | | | | | | | 1.0 | | |
| Sodium Hydroxide (10% sol.) | Sodium Hydroxide | | | 0.3 | 0.6 | 0.4 | | | | | |
| Solubilizer (Symrise) | PEG-40 Hydrogenated Castor Oil, | | | | | | | | | | 2.0 |

-continued

| RAW MATERIAL-NAME (PRODUCER) | | FORMULATION | | | | | | | | | |
|---|---|---|---|---|---|---|---|---|---|---|---|
| | | 4 | 5 | 6 | 7 | 8 | 9 | 10 | 11 | 12 | 13 |
| | Trideceth-9, Water (Aqua) | | | | | | | | | | |
| Sun Flower Oil (Wagner) | Helianthus Annuus (Sunflower) Seed Oil | | | | | | 5.0 | | | | |
| Sweet Almond Oil (Wagner) | Prunus dulcis | | | | | | 5.0 | | | | |
| SymMatrix (Symrise) | Maltodextrin, Rubus Fruticosus (Blackberry) Leaf Extract | | 0.1 | | | 0.3 | 1.0 | | | | |
| Fragrance of Exmaple P2 | Fragrance | 0.3 | 0.3 | 0.3 | 0.2 | 0.4 | 0.4 | 0.5 | 0.3 | 0.3 | 1.0 |
| Tamasterol (Tama Biochemicals) | Phytosterols | | | | | | | | | 0.3 | |
| Tego Betain L7 (Degussa) | Cocamidopropyl Betain | | | | | | | 6.0 | | | |
| Tegosoft PC 31 (Degussa) | | | | | | | | | | 0.3 | |
| Tegosoft TN (Degussa) | C12-15 Alkyl Benzoate | | | 5.0 | | 5.0 | | | | | |
| Triethanolamine | Triethanolamine | | | | | | 0.5 | | | | |
| Tocopherol Acetate (DSM Nutritional Products) | Tocopheryl Acetate | | | 0.5 | | 0.5 | 3.0 | | | 0.3 | |
| Zirkonal L 450 (BK Giulini) | Aluminium Zirconium Pentachlorohydrate (40 wt.-% aqueous solution) | | | | | | | | | | 37.0 |
| Water, demineralized | Water (Aqua) | ad 100 | ad 100 | ad 100 | ad 100 | ad 100 | ad 100 | ad 100 | ad 100 | ad 100 | ad 100 |

Formulation 14-23: Cosmetic formulations comprising a sufficient antimicrobial active amount of
4-methylbenzyl alcohol of formula II
and/or
at least one 1,2-alkanediol.
and/or
at least one further antimicrobial selected from
- (ii) benzoic acid (INCI: Benzoic Acid) and its esters and salts,
- (iii) 4-hydroxybenzoic acid and its esters (INCI: Parabenes) and salts,
- (iv) 2,4-hexadienoic acid (INCI: Sorbic Acid) and its salts,
- (v) 2-phenoxyethanol (INCI: Phenoxyethanol)
- (vi) 3-iodo-2-propinyl-butylcarbamate (INCI: Iodopropynyl Butylcarbamate),
- (vii) 3-(4-chlorphenoxy)-1,2-propane-1,2-diol (INCI: Chlorphenesin), (viii) urea (INCI: Urea) and derivatives thereof, in particular 1,1'-methylen-bis(3-(1-hydroxymethyl-2,4-dioximidazolidin-5-yl))urea (INCI: Imidazolidinyl urea), N-hydroxymethyl-N-(1,3-di(hydroxymethyl)-2,5-dioxoimidazolidin-4-yl)-N'-hydroxymethylurea (INCI: Diazolidinyl Urea) and N-(4-chlorophenyl)-N'-(3,4-dichlorophenyl)-urea (INCI: Triclocarban),
- (ix) 1,3-bis-(hydroxymethyl)-5,5-dimethyl-2,4-imidazolidindione (INCI: DMDM hydantoin),
- (x) 1,2-propanediol, 3-(2-ethylhexyloxy) (INCI: Octoxyglycerin),
- (xi) isothiazolinones and mixtures thereof (e.g. a mixture of 5-chloro-2-methyl-3(2H)-isothiazolinone and 2-methyl-3(2H)-isothiazolinone with magnesium chloride and magnesium nitrate; INCI: Methylchloroisothiazolinone and Methylisothiazolinone)

with formulations 14-23 having the following meaning
- 14=skin lightening day cream O/W
- 15=skin soothing lotion with plant extracts O/W
- 16=after sun balm
- 17=body spray
- 18=broad band sun protection lotion (O/W),
- 19=W/O night cream
- 20=shampoo
- 21=self tanning cream
- 22=barriere repair cream O/W
- 23=antiperspirant//deodorant roll-on

| RAW MATERIAL-NAME (PRODUCER) | INCI | FORMULATION | | | | | | | | | |
|---|---|---|---|---|---|---|---|---|---|---|---|
| | | 14 | 15 | 16 | 17 | 18 | 19 | 20 | 21 | 22 | 23 |
| 4-Methylbenzylalcohol (formula II) | INCI | 0.2 | 0.2 | 0.2 | 0.1 | 0.4 | 0.2 | 0.05 | 0.2 | 1.0 | 0.1 |
| 1,2-Pentanediol (Symrise) | Pentylene Gylcol | | | 3.0 | | | | | | | |
| 1,2-Hexanediol (Symrise) | 1,2-Hexanediol | 0.2 | | | | 0.4 | 0.5 | | | | |
| 1,2-Octanediol (Symrise) | Caprylyl Glycol | 0.6 | | | | | | | | | |
| 1,2-Decanediol (Symrise) | Decylene Glycol | | | | | | | | | 0.5 | |
| Abil 350 (Degussa-Goldschmidt) | Dimethicone | 0.5 | 2.0 | 1.0 | | | | | 0.5 | 0.5 | |
| Allantoin (Merck) | Allantoin | | | 0.2 | 0.1 | | | | | | |
| Aloe Vera Gel Concentrate 10/1 (Symrise) | Water (Aqua), Aloe Barbadensis Leaf Juice | | | 3.0 | | | 3.0 | | | | |
| Alugel 34 TH (Baerlocher) | Aluminium Stearate | | | | | | 1.0 | | | | |
| Aqua-Ceramide (Kao) | Cetyloxypropyl Glyceryl Methoxypropyl Myristamide | | 0.1 | | | | | | | | 0.1 |
| Arbutin (Sabinsa) | β-Arbutin | 1.0 | | | | | | | | | |
| Sodium Ascorbyl (EMD Chemicals) | Sodium Ascorbyl Phosphate | 2.0 | | 1.0 | | | | | | | |
| -(-Alpha-)-Bisabolol, natural (Symrise) | Bisabolol | 0.3 | 0.4 | | | | | 0.05 | | 0.5 | |
| Benzoic Acid | Benzoic Acid | 0.5 | | | | | | | | | |
| Benzoic Acid, 4-hydroxy-, methylester | Methylparaben | | 0.4 | | | | | | | | |
| Benzoic Acid, 4-hydroxy-, ethylester | Ethylparaben | | 0.1 | | | | | | | | |
| Benzoic Acid, 4-hydroxy-, butylester | Propylparaben | | 0.1 | | | | | | | | |
| Benzoic Acid, 4-hydroxy-, isobutylester | Butylparaben | | 0.1 | | | | | | | | |
| Benzyl alcohol | Benzyl Alcohol | | | | 1.0 | | | | | | |
| Butylene Glycol | Butylene Glycol | | | | 5.0 | | | | | | |
| Carbopol ETD 2050 (Noveon) | Carbomer | | | | | | 0.2 | | | | |
| Carbopol Ultrez-10 (Noveon) | Carbomer | | 0.1 | | | | | | | | |
| Ceramide 2 (Sederma) | Ceramide 2 | 0.1 | | | | | | | | | |
| Ceramide PC104 (Pacific Corporation) | Hydroxypropyl Bispalmitamide MEA | | | | | | 0.1 | | | | |
| Ceramide SL (Sino Lion) | Hydroxyethyl Palmityl Oxyhydroxypropyl Palmitamide | | | | | | | 0.1 | | | |
| Cetiol OE (Cognis) | Dicaprylyl Ether | | | 4.0 | | | | | | | |
| Cetiol SB 45 (Cognis) | Butyrospermum Parkii (Shea Butter) | | | 10 | | | | | | | |
| 3-(4-chlorphenoxy)-1,2-propane-1,2-diol | Chlorphenesin | | | | | 0.2 | | | | | |
| Citric Acid 10% sol. | Citric Acid | | | | | | | | 0.3 | | |

-continued

| RAW MATERIAL-NAME (PRODUCER) | | FORMULATION | | | | | | | | |
|---|---|---|---|---|---|---|---|---|---|---|
| | | 14 | 15 | 16 | 17 | 18 | 19 | 20 | 21 | 22 | 23 |
| Comperlan 100 (Cognis) | Cocamide MEA | | | | | | | 0.5 | | | |
| Dihydroxyacetone (Merck) | Dihydroxyacetone | | | | | | | | | 5.0 | |
| Dow Corning 246 Fluid (Dow Corning) | Cyclohexasiloxane and Cyclopentasiloxane | | | | | 2.0 | | | | | |
| Dow Corning 345 Fluid (Dow Corning) | Cyclomethicone | | | | 0.5 | | | | | | |
| D-Panthenol (BASF) | Panthenol | | | 1.0 | | | | | | | |
| Dracorin CE (Symrise) | Glyceryl Stearate Citrate | 5.0 | | | | | | | 5.0 | 1.5 | |
| Dracorin GMS (Symrise) | Glyceryl Stearate | | 2.0 | | | | | | | 2.0 | |
| Dracorin GOC (Symrise) | Glyceryl Oleate Citrate, Caprylic/Capric Triglyceride | | | | 20 | | | | | | |
| Drago-Beta-Glucan (Symrise) | Water (Aqua), Butylene Glycol, Glycerin, Avena Sativa (Oat), Kernel Extract | 0.3 | | | | | | | | | |
| Dragocid Liquid (Symrise) | Phenoxyethanol, Methylparaben, Ethylparaben, Butylparaben, Propylparaben, Isobutylparaben | | 0.8 | 0.7 | | 0.7 | 0.8 | | | 0.8 | |
| Dragoderm (Symrise) | Glycerin, Triticum Vulgare (Wheat) Gluten, Water (Aqua) | | | | | | | 2.0 | | | |
| Drago-Oat-Active (Symrise) | Water (Aqua), Butylene Gylcol, Avena Sativa (Oat) Kernel Extract | | | | | 1.0 | | | | | |
| Dragosan W/O Liquid (Symrise) | Polyglyceryl-3-Polyricinoleate, Sorbitan Isostearate | | | | | | 1.0 | | | | |
| Dragosan W/O P (Symrise) | Sorbitan Isostearate, Hydrogenated Castor Oil, Ceresin, Beeswax (Cera Alba) | | | | | | 6.0 | | | | |
| Dragoxat EH (Symrise) | Ethylhexy Ethylhexanoate | 3.0 | 3.0 | | 4.0 | | | | 3.0 | | |
| Dragoxat 89 (Symrise) | Ethylhexyl Ethylisononanoate | | | | | | | | | 2.0 | |
| EDETA B Pulver (BASF) | Tetrasodium EDTA | | | | | | | 0.1 | | | |
| EDETA DB (BASF) | Disodium EDTA | | | | | 0.1 | | | 0.1 | | |
| Emulsiphos (Symrise) | Potassium Cetyl Phosphate, Hydrogenated Palm Glycerides | | 2.0 | | | 1.5 | | | | 2.0 | |
| Ethanol 96% | Ethanol | | | | | | | | 2.0 | | 30.0 |
| Extrapone Green Tea GW (Symrise) | Glycerin, Water (Aqua), Camellia Sinensis Leaf Extract | | 0.2 | | | | | | | | |
| Extrapone Witch Hazel Distillate colorless | Propylene Glycol, Hamamelis Virginiana (Witch Hazel) Water, | | | | | | 1.0 | | | | |

-continued

| RAW MATERIAL-NAME (PRODUCER) | | FORMULATION | | | | | | | | | |
|---|---|---|---|---|---|---|---|---|---|---|---|
| | | 14 | 15 | 16 | 17 | 18 | 19 | 20 | 21 | 22 | 23 |
| (Symrise) | Water (Aqua), *Hamamelis Virginiana* (Witch Hazel) Extract | | | | | | | | | | |
| Extrapone Rosemary GW (Symrise) | Glycerin, Water (Aqua), *Rosmarinus officinalis* (Rosemary) Leaf Extract | | 0.3 | | | | | | | 0.5 | |
| Farnesol (Symrise) | Farnesol | | | | | | | | | | 0.5 |
| Frescolat ML crist. (Symrise) | Menthyl Lactate | | | 0.8 | | | | | | | |
| Genapol LRO liquid (Cognis) | Sodium Laureth Sulfate | | | | | | | 37.0 | | | |
| Givobio GZN (Seppic) | Zinc Gluconate | | | | | | | | | 0.5 | |
| Glycerin 85% | Glycerin | 3.0 | 2.0 | 4.0 | | 4.7 | 2.0 | | 1.5 | 3.0 | |
| 2,4-Hexadienoic acid | Sorbic Acid | | | | | 0.2 | | | | | |
| Hydroviton (Symrise) | Water, Glycerin, Sodium Lactate, TEA Lactate, Serine, Lactic Acid, Urea, Sorbitol, Sodium Chloride, Lauryl Diethylenediamino glycine, Lauryl Aminopropylglycine, Allantoin | | | | | | | | | 1.0 | |
| N-hydroxymethyl-N-(1,3-di(hydroxymethyl)-2,5-dioxoimidazolidin-4-yl)-N'-hydroxy-methylurea | Diazolidinyl Urea | | | | | | 0.25 | | | | |
| Ingwer CO$_2$ Extrakt (Flavex) | *Zingiber Officinale* (Ginger) Root Extract | 0.003 | | | | | | | | 0.01 | 0.001 |
| 3-Iodo-2-propinyl-butylcarbamate | Iodopropynyl Butylcarbamate | | | | | | | | | | 0.05 |
| Irgasan DP 300 (Ciba Geigy) | Triclosan | | | | | | | | | | 0.3 |
| Isodragol (Symrise) | Triisononanoin | | 2.0 | | | | | | | 3.0 | |
| Isopropylpalmitat (Symrise) | Isopropyl Palmitate | 4.0 | | | | | | | 4.0 | | |
| Karion F (Merck) | Sorbitol | | | | | | 2.0 | | | | |
| Keltrol RD (CP-Kelco) | Xanthan Gum | 0.2 | 0.1 | | | | | | | | |
| Keltrol T (Danby-Chemie) | Xanthan Gum | | | | | 0.2 | | | 0.3 | | |
| Kojic acid (Cosmetochem) | Kojoc acid | 1.0 | | | | | | | | | |
| Lanette 16 (Cognis) | Cetyl Alcohol | 1.0 | | | | | | | 1.0 | | |
| Lanette O (Cognis) | Cetearyl Alcohol | | 3.0 | | | 1.0 | | | | 2.0 | |
| Lara Care A-200 (Rahn) | Galactoarabinan | | | 0.3 | | | | | | | |
| Magnesium Chloride (Merck) | Magnesium Chloride | | | | | | 0.7 | | | | |
| 1,1'-methylen-bis(3-(1-hydroxymethyl- | Imidazolidinyl urea | | | | | | 0.25 | | | | |

-continued

| RAW MATERIAL-NAME (PRODUCER) | | FORMULATION | | | | | | | | | |
|---|---|---|---|---|---|---|---|---|---|---|---|
| | | 14 | 15 | 16 | 17 | 18 | 19 | 20 | 21 | 22 | 23 |
| 2,4-dioximidazolidin-5-yl)urea | | | | | | | | | | | |
| Merquat 550 (Ondeo Nalco) | Polyquaternium-7 | | | | | | | 0.5 | | | |
| NAOH 10% sol. | Sodium Hydroxide | | | | | | | | | 0.3 | |
| Naringin (Exquim) | 4',5,7-Trihydroxyflavon-7-O-neohesperidosid | | | | | | | 0.5 | 2.0 | | |
| Sodium benzoate | Sodium Benzoate | | | | | | | 0.5 | | | |
| Natrosol 250 HHR (Aqualon) | Hydroxyethylcellulose | | | | | | | | | | 0.3 |
| Neo Heliopan 357 (Symrise) | Butyl Methoxy-dibenzoylmethane | | | | | 1.0 | | | | | |
| Neo Heliopan AP (Symrise) (10% solution as Sodium salt) | Disodium Phenyl Dibenzimidazole Tetrasulfonate | | | | | 10 | | | | | |
| Neo Heliopan AV (Symrise) | Ethylhexyl Methoxycinnamate | | | | | 3.0 | | | | | |
| Neo Heliopan Hydro (Symrise) (15% solution as Sodium salt) | Phenylbenzimidazole Sulfonic Acid | | | | | 6.7 | | | | | |
| Neo Heliopan MBC (Symrise) | 4-Methylbenzylidene Camphor | | | | | 1.5 | | | | | |
| Neo Heliopan OS (Symrise) | Ethylhexyl Salicylate | | | | | 5.0 | | | | | |
| Neutral Oil | Caprylic/Capric Triglyceride | 6.0 | | | 4.0 | 2.0 | | | 6.0 | 10.0 | |
| Oxynex 2004 (Merck) | BHT | | | | | | 0.1 | | | | |
| Paraffinöl 5 Grad E (Parafluid) | *Paraffinum Liquidum* | | | | 4.0 | | | | | | |
| PCL Liquid 100 (Symrise) | Cetearyl Ethyl-hexoate | 3.0 | 5.0 | | 7.0 | | | | | | |
| PCL Solid (Symrise) | Stearyl Heptanoate, Stearyl Caprylate | | 2.0 | | | | | | | | |
| PCL-Liquid (Symrise) | Cetearyl Ethyl-hexanoate, Isopropyl Myristate | | | | | | | 12.0 | 3.0 | | |
| Pemulen TR-2 (Noveon) | Acrylates/C10-30 Alkyl Acrylate Crosspolymer | | | 0.3 | 0.2 | | | | | | |
| 2-Phenoxyethanol | Phenoxyethanol | | | | | | | | 1.0 | | |
| 4-(1-Phenylethyl)1,3-benzenediol | 4-(1-Phenylethyl)1,3-benzenediol | 0.5 | | | | | | | | | |
| 1,2-propanediol, 3-(2-ethylhexyloxy | Octoxyglycerin | | | | | | | | | 0.7 | |
| Propylene Glycol-1,2 99P GC | Propylene Glycol | | 5.0 | | | | | | | | |
| Pseudoceramide 391 | N-(1-Hexadecanoyl)-4-hydroxy-L-prolin-(1-hexadecyl-ester | | 0.1 | | | | | 0.2 | | 0.5 | |
| Retinyl Palmitate in Oil (DSM Nutrional Products) | Retinyl Palmitate | | | | | | 0.2 | | | | |
| Sepigel 305 | Polyacrylamide, C13-14 Isoparaffin, Laureth-7 | | | | | | | | 1.0 | | |
| Sodium Chloride | Sodium Chloride | | | | | | | 1.0 | | | |

-continued

| RAW MATERIAL-NAME (PRODUCER) | | FORMULATION | | | | | | | | | |
|---|---|---|---|---|---|---|---|---|---|---|---|
| | | 14 | 15 | 16 | 17 | 18 | 19 | 20 | 21 | 22 | 23 |
| Sodium Hydroxide (10% sol. | Sodium Hydroxide | | 0.3 | 0.6 | 0.4 | | | | | | |
| Solubilizer 611674 (Symrise) | PEG-40 Hydrogenated Castor Oil, Trideceth-9, Water (Aqua) | | | | | | | | | | 2.0 |
| Sun Flower Oil (Wagner) | Helianthus Annuus (Sunflower) Seed Oil | | | | | | 5.0 | | | | |
| Sweet Almond Oil (Wagner) | Prunus dulcis | | | | | | 5.0 | | | | |
| SymMatrix (Symrise) | Maltodextrin, Rubus Fruticosus (Blackberry) Leaf Extract | | 0.1 | | | 0.3 | 1.0 | | | | |
| Fragrance of Exmaple P1 | Fragrance | 0.3 | 0.3 | 0.3 | 0.2 | 0.4 | 0.4 | 0.5 | 0.3 | 0.3 | 1.0 |
| Tamasterol (Tama Bio-chemicals) | Phytosterols | | | | | | | | | 0.3 | |
| Tego Betain L7 (Degussa) | Cocamidopropyl Betain | | | | | | | 6.0 | | | |
| Tegosoft PC 31 (Degussa) | | | | | | | | | | 0.3 | |
| Tegosoft TN (Degussa) | C12-15 Alkyl Benzoate | | | 5.0 | | 5.0 | | | | | |
| Triethanolamine | Triethanolamine | | | | | | 0.5 | | | | |
| Tocopherol Acetate (DSM Nutritional Products) | Tocopheryl Acetate | | | 0.5 | | 0.5 | 3.0 | | | 0.3 | |
| Zirkonal L 450 (BK Giulini) | Aluminium Zirconium Pentachlorohydrate (40 wt.-% aqueous solution) | | | | | | | | | | 37.0 |
| Water, demineralized | Water (Aqua) | ad 100 | ad 100 | ad 100 | ad 100 | ad 100 | ad 100 | ad 100 | ad 100 | ad 100 | ad 100 |

The invention claimed is:

1. A composition comprising:
(a) an effective amount of 4-methylbenzyl alcohol; and
(b) 0.1-5.0 wt.-% of one or more branched or unbranched 1,2-alkanediols having 3 to 14 carbon atoms.

2. The composition according to claim 1, wherein
the composition comprises at least 50 wt.-% of other components besides (a) and (b), and component (a) is present in an amount of from 0.05 to 0.50 wt.-%, based on the total weight of the composition, or
the composition comprises at most 20 wt.-% of other components besides (a) and (b), and component (a) is present in an amount of from 2 to 80 wt.-%, based on the total weight of component (b).

3. The composition according to claim 1, wherein the ratio $r_{a/b}$ of the total weight of component (a) to the total weight of component (b) is in the range of from 1:100 to 5:1.

4. The composition according to claim 1 comprising:
(b) one or more branched or unbranched 1,2-alkanediols having 3 to 10 carbon atoms.

5. The composition according to claim 4, wherein the branched or unbranched 1,2-alkanediols having 3 to 10 carbon atoms are selected from the group consisting of 1,2-propanediol, 1,2-butanediol, 1,2-pentanediol, 1,2-hexanediol, 1,2-octanediol, 1,2-decanediol, and mixtures thereof.

6. The composition according to claim 5 comprising a mixture of branched or unbranched 1,2-alkanediols having 3 to 10 carbon atoms, wherein the mixture is selected from the group consisting of:
a mixture of 1,2-propanediol and 1,2-butanediol,
a mixture of 1,2-propanediol and 1,2-pentanediol,
a mixture of 1,2-propanediol and 1,2-hexanediol,
a mixture of 1,2-propanediol and 1,2-octanediol,
a mixture of 1,2-propanediol and 1,2-decanediol,
a mixture of 1,2-butanediol and 1,2-pentanediol,
a mixture of 1,2-butanediol and 1,2-hexanediol,
a mixture of 1,2-butanediol and 1,2-octanediol,
a mixture of 1,2-butanediol and 1,2-decanediol,
a mixture of 1,2-pentanediol and 1,2-hexanediol,
a mixture of 1,2-pentanediol and 1,2-octanediol,
a mixture of 1,2-pentanediol and 1,2-decanediol,
a mixture of 1,2-hexanediol and 1,2-octanediol,
a mixture of 1,2-hexanediol and 1,2-decanediol,
a mixture of 1,2-octanediol and 1,2-decanediol,
a mixture of 1,2-propanediol, 1,2-pentanediol and 1,2-hexanediol,
a mixture of 1,2-propanediol, 1,2-pentanediol and 1,2-octanediol,
a mixture of 1,2-propanediol, 1,2-hexanediol and 1,2-octanediol,
a mixture of 1,2-pentanediol, 1,2-hexanediol and 1,2-octanediol, a mixture of 1,2-pentanediol, 1,2-octanediol and 1,2-decanediol, a mixture of 1,2-hexanediol, 1,2-octanediol and 1,2-decanediol, a mixture of 1,2-propanediol, 1,2-pentanediol, 1,2-hexanediol and 1,2-octanediol, and a mixture of 1,2-pentanediol, 1,2-hexanediol, 1,2-octanediol and 1,2-decanediol.

7. The composition according to claim 1 comprising:
(b) a mixture of 1,2-hexanediol and 1,2-octanediol.

8. The composition according to claim 1 comprising:
(b) two different 1,2-alkanediols in a weight ratio of from 10:1 to 1:10.

9. The composition according to claim 1, wherein the composition is a cosmetic, a pharmaceutical, an oral care product, a foodstuff, or a beverage.

10. A medicament comprising the composition of claim 1.

11. A method for treating germs comprising contacting a germ with a composition according to claim 1.

12. The method according to claim 11, wherein the germ is *Aspergillus niger*.

13. A method for synergistically intensifying the antimicrobial activity of one or more branched or unbranched 1,2-alkanediol having 3 to 14 carbon atoms comprising mixing:
(a) an effective amount of 4-methylbenzyl alcohol; and
(b) 0.1-5.0 wt.-% of one or more branched or unbranched 1,2-alkanediol having 3 to 14 carbon atoms.

14. A method for preserving a perishable product comprising:
contacting the perishable product with an antimicrobially active amount of a composition according to claim 1.

15. The composition according to claim 1 comprising:
(b) three different 1,2-alkanediols in a weight ratio of from (10 to 60):(10 to 60):(10 to 60).

16. The composition according to claim 1 comprising 4-methylbenzyl alcohol in a mixture with 1,2-hexanediol and 1,2-octanediol, in a weight ratio of from (1 to 2):(1 to 2):(2 to 4).

* * * * *